United States Patent
Joshi et al.

(10) Patent No.: US 12,430,760 B2
(45) Date of Patent: Sep. 30, 2025

(54) REGISTERING INTRA-OPERATIVE IMAGES TRANSFORMED FROM PRE-OPERATIVE IMAGES OF DIFFERENT IMAGING-MODALITY FOR COMPUTER ASSISTED NAVIGATION DURING SURGERY

(71) Applicant: GLOBUS MEDICAL, INC., Audubon, PA (US)

(72) Inventors: Sanjay M. Joshi, Andover, MA (US); Neil Crawford, Chandler, AZ (US); Arjang Noushin, Nashua, NH (US); Ilja Manakov, Munich (DE); Raphael Prevost, Munchen (FR); Matthias Wieczorek, Munich (DE)

(73) Assignee: Globus Medical, Inc., Audubon, PA (US)

( * ) Notice: Subject to any disclaimer, the term of this patent is extended or adjusted under 35 U.S.C. 154(b) by 386 days.

(21) Appl. No.: 17/968,871

(22) Filed: Oct. 19, 2022

(65) Prior Publication Data
US 2023/0123621 A1    Apr. 20, 2023

Related U.S. Application Data

(63) Continuation-in-part of application No. 17/742,463, filed on May 12, 2022.
(Continued)

(51) Int. Cl.
| | | |
|---|---|---|
| G06T 7/00 | (2017.01) | |
| A61B 34/20 | (2016.01) | |
| G06T 3/10 | (2024.01) | |
| G06T 7/55 | (2017.01) | |
| G06T 7/73 | (2017.01) | |

(Continued)

(52) U.S. Cl.
CPC ............ G06T 7/0012 (2013.01); A61B 34/20 (2016.02); G06T 3/10 (2024.01); G06T 7/55 (2017.01); G06T 7/73 (2017.01); G06T 17/20 (2013.01); G06V 10/26 (2022.01); *A61B 2034/2055* (2016.02); *G06T 2207/10081* (2013.01); *G06T 2207/10088* (2013.01);
(Continued)

(58) Field of Classification Search
None
See application file for complete search history.

(56) References Cited

U.S. PATENT DOCUMENTS

| | | |
|---|---|---|
| 4,150,293 A | 4/1979 | Franke |
| 5,246,010 A | 9/1993 | Gazzara et al. |

(Continued)

OTHER PUBLICATIONS

US 8,231,638 B2, 07/2012, Swarup et al. (withdrawn)
(Continued)

*Primary Examiner* — Michelle M Entezari Hausmann

(57) ABSTRACT

A computer platform is provided for computer assisted navigation during surgery. The computer platform includes at least one processor that is operative to transform pre-operative images of a patient obtained from a first imaging modality to an estimate of the pre-operative images of the patient in a second imaging modality that is different than the first imaging modality. The at least one processor is further operative to register the estimate of the pre-operative images of the patient in the second imaging modality to intra-operative navigable images or data of the patient.

18 Claims, 13 Drawing Sheets

Related U.S. Application Data

(60) Provisional application No. 63/319,789, filed on Mar. 15, 2022, provisional application No. 63/257,764, filed on Oct. 20, 2021.

(51) Int. Cl.
    *G06T 17/20* (2006.01)
    *G06V 10/26* (2022.01)

(52) U.S. Cl.
    CPC ............ *G06T 2207/10116* (2013.01); *G06T 2207/20081* (2013.01); *G06T 2207/20084* (2013.01)

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |

(56) References Cited

U.S. PATENT DOCUMENTS

| | | |
|---|---|---|
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Arkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jenser |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,263,933 B2 | 9/2012 | Zeile |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |

(56) References Cited

U.S. PATENT DOCUMENTS

| | | |
|---|---|---|
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Voll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,308,050 B2 | 4/2016 | Kostrzewski et al. |
| 9,380,984 B2 | 7/2016 | Li et al. |
| 9,384,546 B2 * | 7/2016 | Zheng .................. G06T 7/30 |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 12/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |

(56) References Cited

U.S. PATENT DOCUMENTS

| | | |
|---|---|---|
| 11,553,969 B1 * | 1/2023 | Lang .............. G02B 27/0172 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0228117 A1 | 9/2010 | Hartmann |
| 2010/0228265 A1 | 9/2010 | Prisco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |

(56) References Cited

U.S. PATENT DOCUMENTS

| | | |
|---|---|---|
| 2014/0046340 A1 | 2/2014 | Wilson et al. |
| 2014/0049629 A1 | 2/2014 | Siewerdsen et al. |
| 2014/0058406 A1 | 2/2014 | Tsekos |
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0130810 A1 | 5/2014 | Azizian et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Maillet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0020630 A1* | 1/2017 | Johnson ................ A61B 90/96 |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |
| 2020/0286228 A1* | 9/2020 | Guenther ................ G06N 3/08 |
| 2021/0386391 A1* | 12/2021 | Karanam ............... A61B 6/461 |
| 2022/0092771 A1* | 3/2022 | Itu ........................ G06T 7/0012 |

OTHER PUBLICATIONS

Guan, Shaoya, et al. "Deformable cardiovascular image registration via multi-channel convolutional neural network." IEEE Access 7 (2019): 17524-17534. (Year: 2019).*

Barillot, Christian, et al. "PC software package to confront multimodality images and a stereotactic atlas in neurosurgery." Medical Imaging IV: Image Capture and Display. vol. 1232. SPIE, 1990. (Year: 1990).*

Hou, Benjamin, et al. "3-D reconstruction in canonical co-ordinate space from arbitrarily oriented 2-D images." IEEE transactions on medical imaging 37.8 (2018): 1737-1750. (Year: 2018).*

Shang, Kai, Xiaoyue Li, and Mark D. Butala. "A Style-Based Model for MRI to CT Image Translation." 2023 9th International Conference on Computer and Communications (ICCC). IEEE, 2023. (Year: 2023).*

Azampour, M. F., Mach, K., Fatemizadeh, E., Demiray, B., Westenfelder, K., Steiger, K., . . . & Navab, N. (2024). Multitask Weakly Supervised Generative Network for MR-US Registration. IEEE Transactions on Medical Imaging. (Year: 2024).*

Chen et al. "Unsupervised multi-modal style transfer for cardiac MR segmentation." STACOM 2019, Held in Conjunction with MICCAI 2019, Shenzhen, China, Oct. 13, 2019 (Year: 2019).*

Miao, Xuan, et al. "Post-operative MRI synthesis from pre-operative MRI and post-operative CT using conditional GAN for the assessment of degree of resection." Displays 83 (2024): 102742. (Year: 2024).*

Li, Zhihua, et al. "Medical Multi-Modal Image Transformation With Modality Code Awareness." IEEE Transactions on Radiation and Plasma Medical Sciences (2024). (Year: 2024).*

Ku, Ping-Cheng, et al. "Towards 2D/3D registration of the preoperative MRI to intraoperative fluoroscopic images for visualisation of bone defects." Computer Methods in Biomechanics and Biomedical Engineering: Imaging & Visualization 11.4 (2023): 1096-1105. (Year: 2023).*

Feng, Yidan, et al. "Bridging MRI Cross-Modality Synthesis and Multi-Contrast Super-Resolution by Fine-Grained Difference Learning." IEEE Transactions on Medical Imaging (2024). (Year: 2024).*

El Hadramy, Sidaty, et al. "Intraoperative CT augmentation for needle-based liver interventions." International Conference on Medical Image Computing and Computer-Assisted Intervention. Cham: Springer Nature Switzerland, 2023. (Year: 2023).*

* cited by examiner

REGISTERING INTRA-OPERATIVE IMAGES TRANSFORMED FROM PRE-OPERATIVE IMAGES OF DIFFERENT IMAGING-MODALITY FOR COMPUTER ASSISTED NAVIGATION DURING SURGERY

CROSS REFERENCE TO RELATED APPLICATION

This application claims the benefit of U.S. Provisional Patent Application No. 63/319,789, filed on Mar. 15, 2022, and further claims the benefit of U.S. Provisional Patent Application No. 63/257,764, filed on Oct. 20, 2021, the disclosure and content of which are incorporated by reference herein in their entirety.

The present application is also a continuation-in-part of U.S. patent application Ser. No. 17/742,463, filed May 12, 2022, the disclosure and content of which are incorporated by reference herein in their entirety.

FIELD

The present disclosure relates to medical devices and systems, and more particularly, camera tracking systems used for computer assisted navigation during surgery.

BACKGROUND

A computer assisted surgery navigation system can provide a surgeon with computerized visualization of how a surgical instrument that is posed relative to a patient correlates to a pose relative to medical images of the patient's anatomy. Camera tracking systems for computer assisted surgery navigation typically use a set of cameras to track pose of a reference array on the surgical instrument, which is being positioned by a surgeon during surgery, relative to a patient reference array (also "dynamic reference base" (DRB)) affixed to a patient. The camera tracking system uses the relative poses of the reference arrays to determine how the surgical instrument is posed relative to a patient and to correlate to the surgical instrument's pose relative to the medical images of the patient's anatomy. The surgeon can thereby use real-time visual feedback of the relative poses to navigate the surgical instrument during a surgical procedure on the patient.

SUMMARY

Some embodiments of the present disclosure are directed to a method that includes transforming pre-operative images of a patient obtained from a first imaging modality to an estimate of the pre-operative images of the patient in a second imaging modality that is different than the first imaging modality. The method further includes registering the estimate of the pre-operative images of the patient in the second imaging modality to intra-operative navigable images or data of the patient.

Some other corresponding embodiments of the present disclosure are directed to a computer platform is provided for computer assisted navigation during surgery. The computer platform includes at least one processor that is operative to transform pre-operative images of a patient obtained from a first imaging modality to an estimate of the pre-operative images of the patient in a second imaging modality that is different than the first imaging modality. The at least one processor is further operative to register the estimate of the pre-operative images of the patient in the second imaging modality to intra-operative navigable images or data of the patient.

Other methods and corresponding computer platforms according to embodiments of the inventive subject matter will be or become apparent to one with skill in the art upon review of the following drawings and detailed description. It is intended that all such additional methods and corresponding computer platforms be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1:
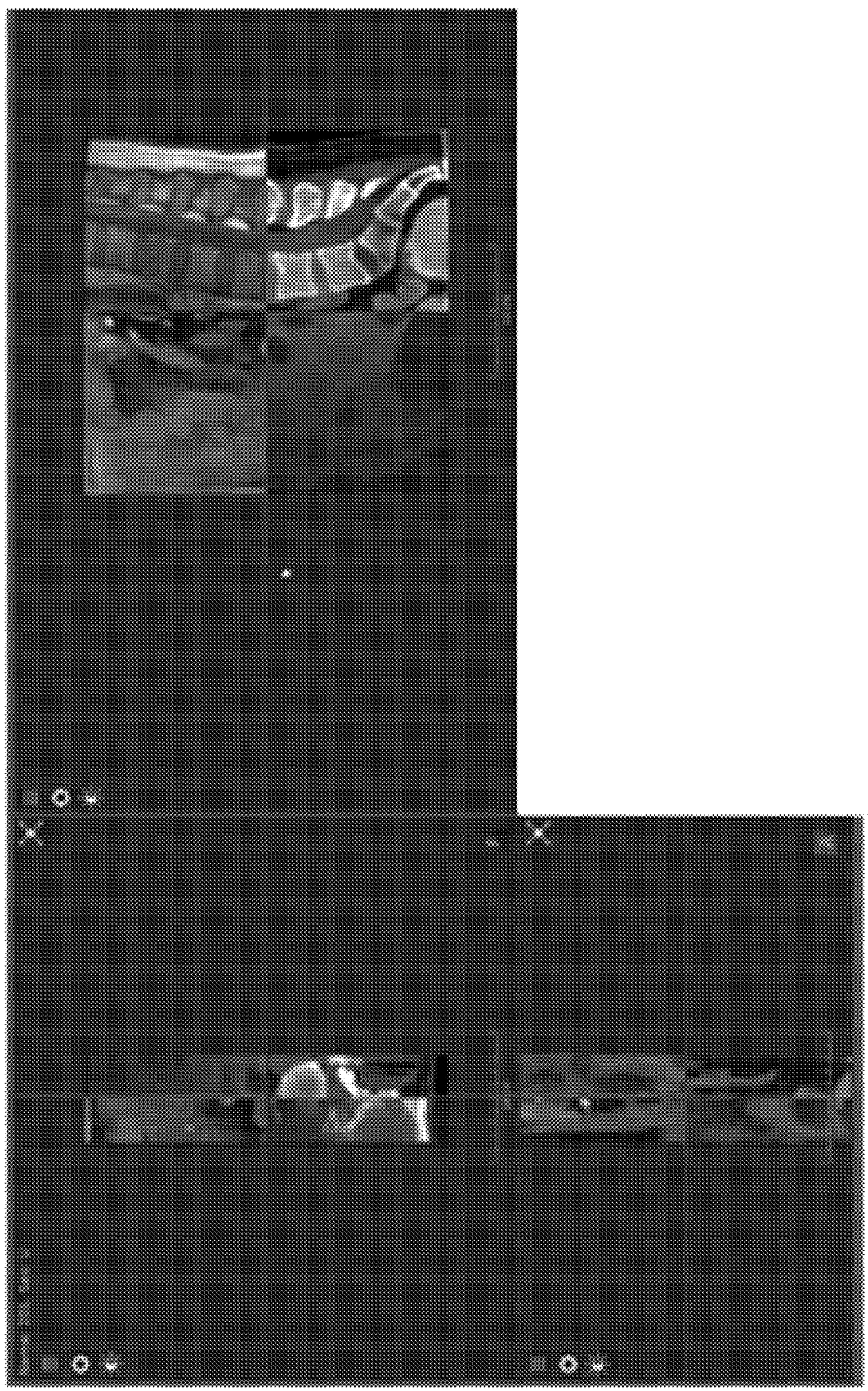
FIG. 1 illustrates a set of synthetic computerized tomography (CT) images of a patient that have been created through transformation of pre-operative magnetic resonance imaging (MRI) image(s) of the patient for registration to intra-operative navigable CT images of the patient in accordance with some embodiments of the present disclosure.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Various embodiments of the present disclosure are directed to methods for registering pre-operative images of a patient from one or more modalities to intra-operative navigable images or data of the same patient using an imaging modality that may or may not be present in the pre-operative image set is disclosed. Recent advances in machine learning allow estimating the images of intra-operative modality to allow such registration. Once registered, the pre-operative images can be used for surgical navigation.

Registration of medical images from one imaging modality with those from another imaging modality can be used in computer assisted surgeries. Such registrations allow comparison of anatomical features and enable intra-operative navigation even on images from imaging modalities not present in the operating room. A common example is registration of pre-operative computerized tomography (CT) images to intra-operative fluoroscopy (fluoro) images.

In the current pre-op CT robotic/navigation workflow, a preoperative 3D CT is registered to the tracking camera's coordinate system using a pair of 2D tracked fluoro images. For each fluoro image, the location of the image plane and emitter are optically tracked via a fixture attached to the fluoro unit. The algorithm works by generating synthetic fluoro shots (digitally reconstructed radiographs (DRRs)) mathematically by simulating the x-ray path through the CT volume. When a match is found between the actual x-ray images and DRRs, registration is achieved because the locations of the image plane and emitter are simultaneously known relative to the CT volume and relative to the cameras.

The term synthetic image is used herein to refer to an image that is an estimate or approximation of an image that would be obtained through a particular imaging modality. For example, a synthetic X-ray image can be generated from a magnetic resonance imaging (MRI) image of a patient to provide an estimate or approximation of what an X-ray image would have captured if an X-ray imaging modality had been performed on the patient.

A key part of the above algorithm for registering the CT image to the tracking cameras is the ability to generate a DRR from the CT image to compare against the actual x-ray. It is fairly straightforward to generate a DRR from a CT volume because CT images are themselves comprised of x-ray image voxels. If other imaging modalities could be used to generate a synthetic x-ray, then they too could be used for registration and navigation. For example, if an MRI volume could be used to generate a DRR, then a pair of tracked x-rays could also be used to register an MRI volume to a tracking camera and navigation could be performed relative to an MRI image.

Or, considering the 2D registration images instead of the 3D reference image volume, a CT image volume could be registered to a pair of ultrasound poses or other two-dimensional images if the 2D counterpart to the image—e.g., synthetic ultrasound image—can be generated from the CT volume.

The first inter-modality registration method uses MRI instead of CT to generate synthetic fluoro shots (DRRs). One approach to this problem is to convert the MR images first to a CT-like appearance and then to convert the CT images to DRRs. MR images can be "mapped" to CT images in some respects, but there are some parts of the image content that are not just simply mapped and require more advanced prediction to show correctly. Artificial intelligence (AI) can be used to perform modality synthesis by predicting how different regions of the MRI should appear if it is to look like a CT. A neural networks model can be trained by using matched sets of images of the same anatomy taken with both MR and CT. From this training, the model learns what image processing steps it needs to take to accurately convert the MR to a CT-like appearance, and then the processed MRI can be further processed in the same way as the CT is currently processed to create the DRRs.

Another approach to the modality synthesis problem is to use a neural networks model to directly convert the MR to a DRR without requiring an intermediate step of first creating a CT-like appearance. A neural networks model can be trained by registering a MR image volume to a tracking camera coordinate system based on, for example, a known technique such as point matching, and then taking tracked x-ray shots of the anatomy, using the tracking information to determine the path that the x-rays took through the MRI volume. For point matching, fiducials that are detectable both on MRI and also to the tracking system are needed, such as Vitamin E spheres that can be touched by a tracked probe or tracked relative to a fixture and detected within the image volume.

An alternative technique to register a MR image volume to a tracking camera coordinate system is to get a cone beam CT volume of a patient or cadaver that is tracked with a reference array using a system such as O-arm or E3D. Using the mapping technique of these devices, the coordinate system of the CT and tracking cameras are auto registered. Then, the MRI volume can be registered to the CT volume using image-image registration with matching of bony edges of the CT and MRI such as is currently done in the cranial application. Because the MRI is registered to tracking, the locations of the synthetic image (DRR) plane and theoretical emitter relative to the MRI are known and the model can learn how to convert the MR image content along the x-ray path directly to a DRR.

Both technique described above may require or benefit from the MRI image having good resolution in all dimensions, without which it is difficult to operationally visualize the curved bone surfaces from multiple perspectives. This requirement may be problematic with standard MRI sets that are acquired clinically. Typically, MRI sets acquired clinically have good resolution in one plane but poor resolution in and out of this plane. For example, a MRI scan that may show submillimeter precision on each sagittal slice acquired, but each sagittal slice may be several millimeters from the next sagittal slice, so viewing the reconstructed volume from a coronal or axial perspective would appear grainy.

FIG. 1 illustrates a set of synthetic CT images of a patient that have been created through transformation of pre-operative MRI image(s) of the patient for registration to intra-operative navigable CT images of the patient in accordance with some embodiments of the present disclosure. More particularly, a reconstructed volume from MRI imaging modality has been transformed to create a CT-like appearance in diagonal tiles of a checkerboard layout using a set of sagittal slices. Sagittal plane resolution is relatively high, e.g., <1 mm, in the right picture. However, because the inter-slice distance is relatively large (~5 mm) the resolution in axial and coronal views in the left pictures is relatively poor.

Often, a set of images for a patient could include one set of slices with high resolution in one plane (e.g., sagittal) and another set of slices for the same patient with high resolution in another plane (e.g., axial). Since these two sets of slices are taken at different times and the patient may have moved slightly, it is difficult to merge the sets into a single volume with high resolution in all directions. In one embodiment the system enables vertebra-by-vertebra registration to merge two low-resolution volumes into a higher resolution volume.

In another embodiment, to improve the grainy appearance from side-on views of a low-resolution MR is to use the interpolated image content, or predicted CT-like appearance, in addition to the final voxel contrast to improve the resolution in the side dimension since the prediction may not be purely linear from voxel to voxel. If this technique of image processing is applied to each vertebra from a sagittal view and also from an axial view, it may be possible to get adequate bone contour definition to perform a deformable registration to move each vertebra from one perspective into exact alignment with the corresponding vertebra from the other perspective. For example, the reconstructed volume from sagittal slices could be used as the reference volume, and then each vertebra reconstructed from sagittal slices could be individually adjusted in its position and rotation to perfectly overlay on the corresponding vertebra in the reference volume. After vertebra-by-vertebra registration, the two volumes would be merged to create a new volume that has high definition in all 3 dimensions.

For a registration technique where the modality of a tracked ultrasound (US) probe is used to provide the reference 2D images for registration with CT or MRI, an AI approach can again be used. In this approach, a machine learning model (such as a neural networks model) is trained with ground truth data from a CT or MR image volume that has already been registered by another technique such as point matching with appropriate fixtures and fiducials. The exact location and orientation of the optically tracked probe if acquired, and the corresponding location of the probe relative to the CT or MRI volume is obtained through the use of the point match registration or with a tracked and auto-registered CBCT scan (also registered to MRI if desired). In some embodiments, the neural networks model is trained using the US image and the voxel-by-voxel data from the CT or MRI that would be intersected by the US wave passing through the tissues from that known perspective, to teach the neural networks model to generate a synthetic US image for future registration. Once the neural networks model can generate a synthetic US image from the MRI or CT data, it is used in future cases to determine where the tracked US probe must have been located at the time the US image was taken, and therefore to register the tracking cameras to the MRI or CT volume for use in providing computer assisted navigation relative to the MRI or CT volume during surgery.

In some other embodiments, images from an intra-operative MRI are registered with pre-operative MRI. Due to differences in field strengths, fields of view, system characteristics, and pulse sequence implementation differences, anatomical features in images from pre-operative MRIs may not match those in the intra-operative MRI. A neural network model neural networks model is trained to process MRI images from different imaging modalities, e.g., different medical scanners of the same of different types, to achieve cross-registration and allow surgical navigation using pre-operative MRI images. This technique can be used not just for 3D MRI scans, but also for 2D MRI scans which are typically multi-planar slices through the volume and not a 'summative' projection as obtained by x-rays. The registration operations may be further configured to provide visualization of intra-operative anatomical shifts, e.g., brain shifts.

In some other embodiments, the techniques described above can be configured to register MRI and CT scans to images from optical cameras. MRI and/or CT images are processed to generate a synthetic optical surface, e.g., skin surface, which is registered with images from optical cameras, e.g., optical light cameras.

Some further embodiments are directed to creating completely synthetic images that are purely virtual. In some embodiments, MRI images and/or CT images are used to create synthetic images of tissues that show a contrast not visible in any of the source images. Examples embodiments include generating synthetic scans that can show only neurons and blood vessels to allow a surgeon to visualize different surgical approaches or only discs between the vertebrae.

Potential advantages that may be obtained by one or more of these embodiments may include one or more of the following:
1) Reduced radiation since a MRI volume can be used for registration instead of CT;
2) Reduced cost since ultrasound can be used instead of X-rays;
3) Ability to track real-time changes such as brain shift;
4) Ability to use visible light images for registration with other imaging modalities; and
5) Ability to construct purely synthetic images that show a contrast which cannot be obtained by conventional imaging modalities.

Figure 2:
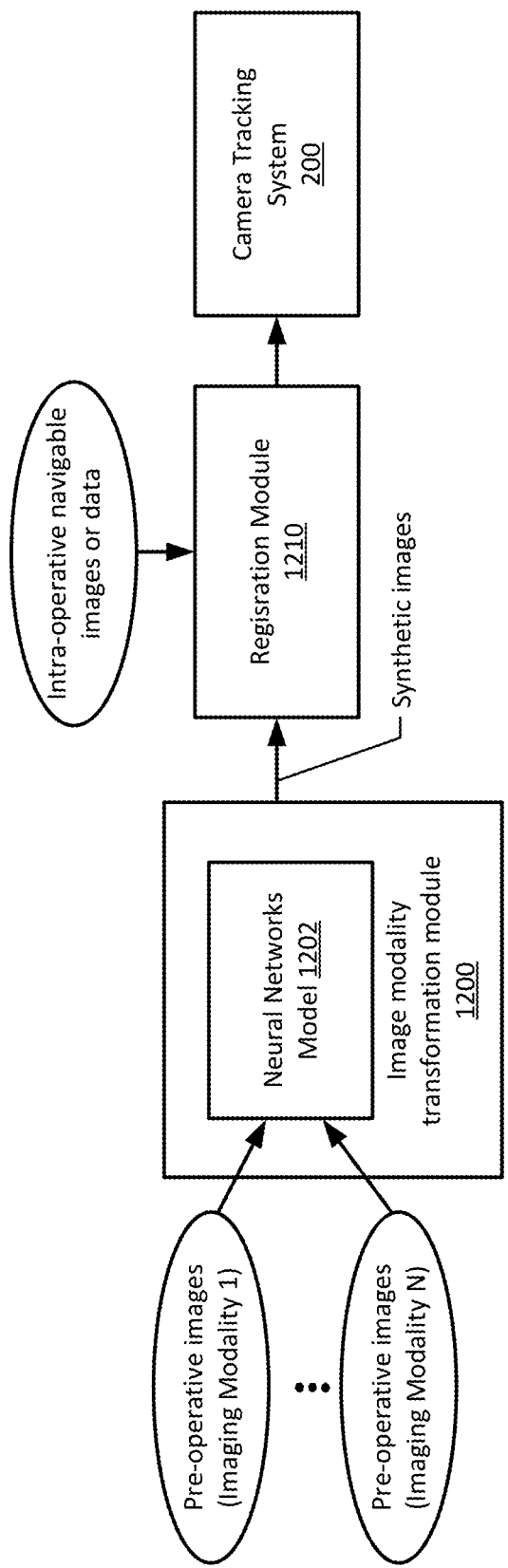
FIG. 2 illustrates a computer platform that is configured to operate in accordance with some embodiments.

FIG. 2 illustrates a computer platform (e.g., platform 400 in FIG. 11) that is configured to operate in accordance with some embodiments. The computer platform accesses pre-operative images obtained from one or more imaging modalities, such as MRI modality, CT imaging modality, ultrasound imaging modality, etc. An image modality transformation module 1200 transforms the pre-operative images of a patient obtained from a first imaging modality to an estimate, which can also be referred to as synthetic images, of the pre-operative images of the patient in a second imaging modality that is different than the first imaging modality. In some embodiments, the module 1200 includes one or more neural networks model(s) 1202 which can be configured according to various embodiments described below. A registration module 1210 is configured to register the estimate of the pre-operative images of the patient in the second imaging modality to intra-operative navigable images or data of the patient. The intra-operative navigable images or data of the patient are obtained by the second imaging modality, and may be obtained from a CT imaging device, ultrasound imaging device, etc. The intra-operative navigable images or data of the patient are registered to a coordinate system that is tracked by a camera tracking system 200 which is further described below with regard to FIGS. 8 through 11.

In some further embodiments, the operation to transform the pre-operative images of the patient obtained from the first imaging modality to the estimate of the pre-operative images of the patient in the second imaging modality, includes to process the pre-operative images of the patient obtained from the first imaging modality through the neural networks model 1202. The neural networks model 1202 is configured to transform pre-operative images in the first imaging modality to estimates of the pre-operative images in the second imaging modality. The neural networks model 1202 has been trained based on matched sets of training images containing anatomical features captured by the first imaging modality and training images containing anatomical features captured by the second imaging modality, wherein at least some of the anatomical features captured by the first imaging modality correspond to at least some of the anatomical features captured by the second imaging modality.

In some further embodiments, the operations perform the training of the neural networks model 1202 based on matched sets of training images containing anatomical features captured by the first imaging modality and training images containing anatomical features captured by the second imaging modality.

In some further embodiments, the operation to transform the pre-operative images of the patient obtained from the first imaging modality to the estimate of the pre-operative images of the patient in the second imaging modality, includes to transform pre-operative MRI images of the patient to synthetic x-ray images of the patient. The operation to register includes to register the synthetic x-ray images of the patient to intra-operative navigable x-ray images of the patient, wherein the intra-operative navigable x-ray images are registered to a coordinate system of a camera tracking system.

In some further embodiments, the operation to transform the pre-operative MRI images of the patient to the synthetic x-ray images of the patient, includes to transform the pre-operative MRI images of the patient to synthetic CT images of the patient, and to transform the synthetic CT images of the patient to the synthetic x-ray images. The operation to transform the pre-operative MRI images of the patient to the synthetic CT images of the patient, may include to processing the pre-operative MRI images of the patient through a neural networks model 1202 configured to transform pre-operative MRI images to synthetic CT images. The neural networks model 1202 may have been trained based on matched sets of training MRI images containing anatomical features captured by MRI modality and training CT images containing anatomical features captured by CT imaging modality. At least some of the anatomical features captured by the MRI modality correspond to at least some of the anatomical features captured by the CT imaging modality.

In some further embodiments, the operations further include to: obtain a first slice set of pre-operative MRI images of the patient having higher resolution in a first plane and a lower resolution in a second plane orthogonal to the first plane; obtain a second slice set of pre-operative MRI image slices of the patient having higher resolution in the second plane and a lower resolution in the first plane; and merge the first and second slice sets of pre-operative MRI images by registration of anatomical features captured in both of the the first and second slice sets of pre-operative MRI images, to output a merged slice set of pre-operative MRI images. The merged slice set of pre-operative MRI images are processed through the neural networks model for transform to the synthetic CT images.

In some further embodiments, the operations to transform the pre-operative images of the patient obtained from the first imaging modality to the estimate of the pre-operative images of the patient in the second imaging modality, include to transform pre-operative MRI images or CT images of the patient to synthetic ultrasound images of the patient. The operations to register include to register the synthetic ultrasound images to intra-operative navigable ultrasound images of the patient, wherein the intra-operative navigable ultrasound images are registered to a coordinate system of a camera tracking system.

In some further embodiments, the operations to transform the pre-operative MRI images or the CT images of the patient to the synthetic ultrasound images of the patient, include to process the pre-operative MRI images or CT images of the patient through a neural networks model 1202 that is configured to transform pre-operative MRI images or CT images to synthetic ultrasound images. The neural networks model 1202 has been trained based on matched sets of: 1) training ultrasound images; and 2) either training MRI images or training CT images. The matched sets of: 1) training ultrasound images; and 2) either training MRI images or training CT images, have defined correspondences between anatomical features captured in images of the matched sets.

In some further embodiments, the operations to transform the pre-operative images of the patient obtained from the first imaging modality to the estimate of the pre-operative images of the patient in the second imaging modality, includes to transform pre-operative MRI images or CT images of the patient to synthetic optical camera images of the patient. The operations to register include to register the synthetic optical camera images to intra-operative navigable optical camera images of the patient, wherein the intra-operative navigable optical camera images are registered to a coordinate system of a camera tracking system.

In some further embodiments, the operations to transform the pre-operative MRI images or CT images of the patient to the synthetic optical camera images of the patient, include to process the pre-operative MRI images or CT images of the patient through a neural networks model 1202 configured to transform pre-operative MRI images or CT images to synthetic optical camera images. The neural networks model 1202 has been trained based on matched sets of: 1) training optical camera images; and 2) either training MRI images or training CT images. The matched sets of: 1) training optical camera images; and 2) either training MRI images or training CT images, have defined correspondences between anatomical features captured in images of the matched sets.

Some other embodiments are now described which are directed to related systems and methods of converting Magnetic Resonance Imaging (MRI) modality data to Computed Tomography (CT) modality data using a neural network.

Some further embodiments are directed to using neural networks to generate synthesized CT images from MRI scans. Successfully generating synthetic CTs enables clinicians to avoid exposing their patients to ionizing radiation while maintaining the benefits of having a CT scan available. Some embodiments can be used in combination with various existing CT-based tools and machine learning models. In some embodiments, a generative adversarial network (GAN) framework (GANs'N'Roses) is used to split the input into separate components to explicitly model the difference between the contents and appearance of the generated image. The embodiments can introduce an additional loss function to improve this decomposition, and use operations that adjust the generated images to subsequent algorithms with only a handful of labeled images. Some of the embodiments are then evaluated by observing the performance of existing CT-based tools on synthetic CT images generated from real MR scans in landmark detection and semantic vertebrae segmentation on spine data. The framework according to some of these embodiments can outperform two established baselines qualitatively and quantitatively.

Although various embodiments are described in the context of using neural networks models to transform between imaging modalities, these and other embodiments may more generally be used with other types of machine learning models. Embodiments that use a neural networks model for transformations between imaging modalities may benefit for the ability of neural networks model to be configured to simultaneously process an array of input data, e.g., part or all of an input image, to output transformed array of data, e.g., transformed part of all of the input image.

1. INTRODUCTION

Due to its short acquisition times and high 3D resolution, CT has always been a staple in medical imaging. Its quantitative nature eases data comparison and collection across scanner manufacturers and clinical sites. the medical imaging analysis, machine learning models and algorithms can be used to generalize to new datasets. As such, recent years have seen a plethora of publications exploring deep-learning-based methods for various clinical tasks on CT images. However, the ionizing radiation used in CT poses a significant disadvantage, especially in pediatric cases or when examining organs-at-risk. Magnetic resonance imaging (MRI), on the other hand, constitutes another widespread imaging modality and avoids the dangers of ionizing radiation while simultaneously offering superior soft-tissue contrast. Yet bony structures, which have high contrast in CT, are not visible in MRI.

Various embodiments are directed to leveraging advancements in machine learning to synthesize images or data in one imaging modality from images or data in another modality, such as to synthesize CT images from existing MRI scans. A motivation is to use the synthetic CTs (sCT) in downstream tasks tailored to the CT modality (e.g., image segmentation, registration, etc.). As will detail in Section 2, a given MRI image can have multiple valid CT counterparts that differ in their acquisition parameters (dose, resolution, etc.) and vice versa. Single-output neural networks models have difficulties learning the distinction between the anatomical content and its visual representation. Some embodiments of the present disclosure build upon an architecture disclosed in a paper by Chong et al. [3] named GANs'N-'Roses (GNR), that allows the neural networks models to separate these two concepts. The processing architecture separates content aspects from style aspects, where content refers to "where landmarks (anatomical features) are located in an image" and style refers to "how landmarks (anatomical features) look in an image". This distinction enables the generation of sCTs with the same content but different appearances by utilizing multiple styles.

In some embodiments of the present disclosure, operations can use the GNR model for synthesizing CTs from MR images of the spine and compare it to the established baseline models. These operations do not necessarily evaluate the sCTs by themselves but rather can use sCTs with existing CT tools on the tasks of key-point detection and semantic vertebrae segmentation. The embodiments also extend the GNR framework by adding a loss function that follows a similar logic as the style regularization in [3] to emphasize the separation of content and style further. Additionally, embodiments of the present disclosure can be directed to a low-cost, e.g., lower processing overhead and/or processing time, operations for fine-tuning the appearance of generated images to increase the performance in downstream tasks that requires only a handful of labeled examples.

2. RELATED WORK

Several approaches [19, 5, 13, 12] for generating synthetic CTs require paired registered MRI and CT data as they rely on directly minimizing the pixel-wise difference between the synthetic and real CT. While paired datasets provide a strong supervisory signal to the model, the time and money required to generate such paired data can be problematic. These factors may explain why no such dataset is known to be publicly available. A new set of operations based on consistency criteria, such as the cycle consistency loss introduced by Zhu et al. [18], paved the way for working with unpaired datasets. Wolternik et al. [15] showcased the potential impact of imperfect registrations between CT and MRI by training a cycle-consistent GAN (CycleGAN) [18] and comparing it to the same generator network trained in a supervised way on registered cranial CT and MRI data. The CycleGAN outperformed the supervised model in that study in terms of MAE and peak signal-to-noise ratio. Chartsias et al. [2] used a CycleGAN to generate synthetic MRI images from cardiac CT data. Several papers [16, 1, 7] however, reported on structural inconsistencies resulting from CycleGAN, which they attempted to solve using additional loss terms during training, e.g., of the neural networks model. Other works leveraged manual segmentations to induce structural consistency; Zhang et al. [17] for sCT generation via CycleGAN, Tomar et al. [14] for generation of realistic-looking ultrasound images from simulated ones using a Contrastive Unpaired Translation (CUT) model [10]. In practice, however, consistency-based methods do not guarantee the structures (i.e., the anatomical information) to be preserved, as generators tend to encode information as high-frequency patterns in the images [4]. The publication by Karthik et al. [8] attempts unpaired MRI-to-CT translation on spine data. Unfortunately, the evaluation is limited, and the authors report manually correcting the spine segmentations obtained by thresholding the sCTs, making it inconclusive.

3.1 Modality Synthesis Using GNR

Various embodiments of the present disclosure can be based on extending some of the operations disclosed in the paper GANs'N'Roses by Chong et al. [3] from the computer vision literature. Some embodiments operate to combine two GANs into a circular system and use cycle consistency as one of its losses, while adapting an architecture and regularization of the generator networks.

Figure 3:
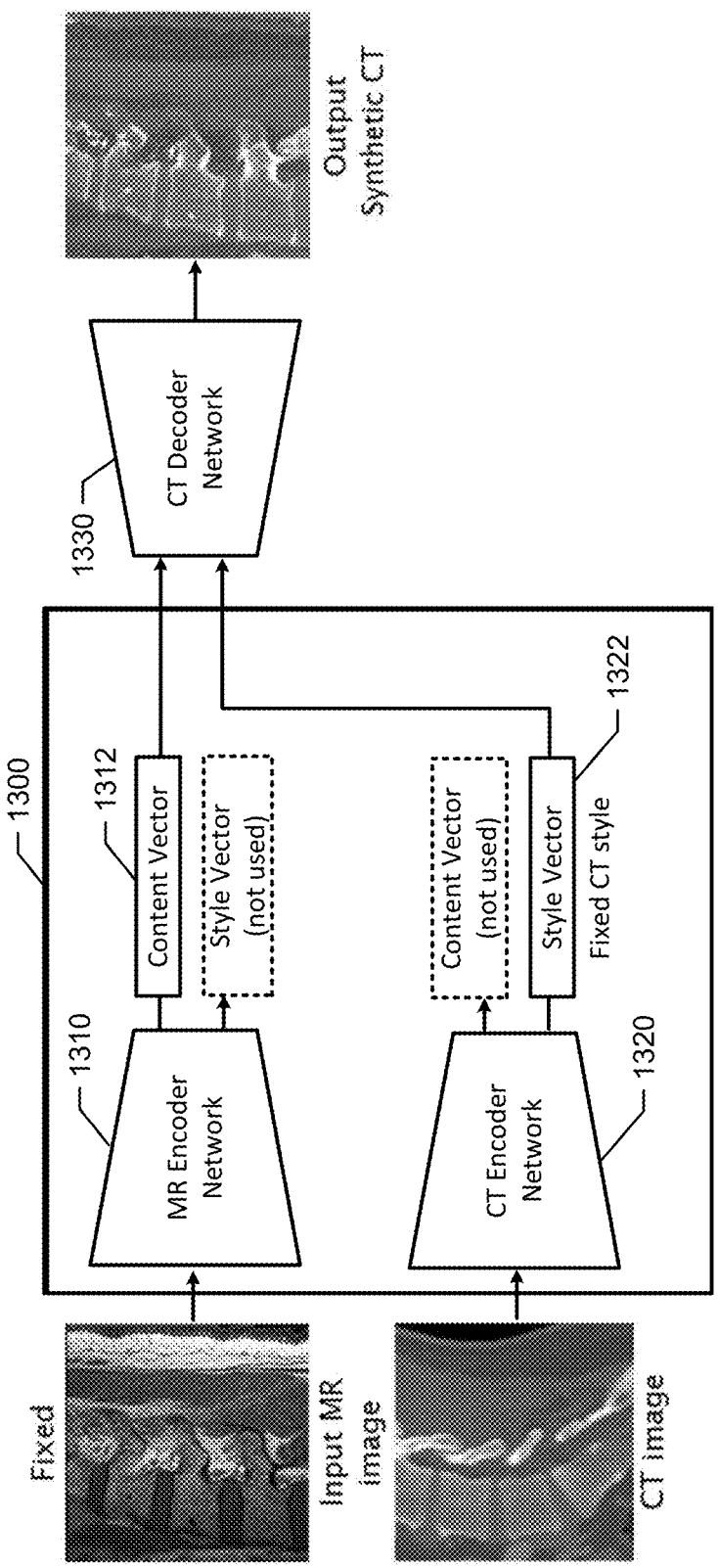
FIG. 3 illustrates a functional architecture for MR-to-CT modality synthesis in accordance with some embodiments.

FIG. 3 illustrates a functional architecture for MR-to-CT modality synthesis in accordance with some embodiments. Referring to FIG. 3, the architecture is divided into an encoder E=(Ec, Es) 1300 and a decoder 1330. The encoder E 1310 splits the input image into a content component c (also called "content vector") and a style s component (also called "style vector"). The decoder D 1330 uses these components to generate a synthetic image.

To bias the model to learn the desired distinction between content and style, training loss are performed, which are referred to as style consistency loss. From every training batch $B^{tr}$, the network picks a random sample, duplicates it to match the number of samples in the batch, and augments each duplicate with style-preserving transformations as (random affine transformations, zooming, and horizontal flipping). Since all samples in the augmented batch originate from the same image and since the augmentations only change the location of things in the image, i.e., content ("where landmarks are"), but not their appearance, i.e., style ("what landmarks look like"), the styles of the samples in this augmented batch $B^{aug}$ should be the same. As such, the style consistency loss can be based on the following:

$$L_{sc} = \text{var}(E_s(B^{aug})), \text{with } B_i^{aug} = a_s(B_j^{tr}), i=1,\ldots,|B^{tr}|, j \in \{1, |B^{tr}|\} \quad (1)$$

In the example of FIG. 3, the training batch of input MR images are encoded by a MR encoder network 1310, e.g., a neural network configured to encode MR images, to output the content component (content vector) 1312, while a style component (style vector) is not used. Similarly, the training batch of CT images are encoded by a CT encoder network 1320, e.g., a neural network configured to encode CT images, to output the style component (style vector) 1322, while a content component (content vector) is not used.

At inference time, operations for generating a synthetic image include encoding the input with the encoder of its native domain (either MR encoder network 1310 or CT encoder network 1320), keeping the content component, and decoding it using the decoder 1330 and a style from the other domain. In the example of FIG. 3, the output synthetic CT images may be generated by: 1) encoding the input MR images through the MR encoder network 1310 to output the content component (content vector) 1312 of the MR images; 2) encoding the input CT images through the CT encoder network 1320 to output the style component (style vector) 1322 of the CT images; and 3) decoding the content component (content vector) 1312 of the MR images using the style component (style vector) 1322 of the CT images.

Corresponding operation that can be performing by a computing platform to the transform pre-operative images of a patient obtained from a first imaging modality to an estimate of pre-operative images of the patient in a second imaging modality are now further described in accordance with some embodiments. The operations include to encode pre-operative image of the patient obtained from the first imaging modality to output a content vector indicating where anatomical features are located in the pre-operative images of the first imaging modality. The operations encode pre-operative images of the patient obtained from the second imaging modality to output a style vector indicating how the anatomical features look in the pre-operative images of the second imaging modality. The operations decode the content vector indicating where the anatomical features are located in the pre-operative images of the first imaging modality using the style vector indicating how the anatomical features look in the pre-operative images of the second imaging modality. The operations generate the estimate of the pre-operative images of the patient in the second imaging modality based on an output of the decoding.

The first and second imaging modalities are different, and may be different ones of: magnetic resonance imaging (MRI) modality; computerized tomography (CT) imaging modality; and ultrasound imaging modality.

In some further embodiments, the operations to encode the pre-operative image of the patient obtained from the first imaging modality to output the content vector indicating where anatomical features are located in the pre-operative images of the first imaging modality, include to process the pre-operative image of the patient in the first imaging modality through a first neural networks model that is configured to output the content vector indicating where anatomical features are located in the pre-operative images of the first imaging modality. The operations to encode the pre-operative images of the patient obtained from the second imaging modality to output the style vector indicating how the anatomical features look in the pre-operative images of the second imaging modality, include to process the pre-operative images of the patient obtained from the second imaging modality through a second neural networks model that is configured to output the style vector indicating how the anatomical features look in the pre-operative images of the second imaging modality. The operations to decode the content vector indicating where the anatomical features are located in the pre-operative images of the first imaging modality using the style vector indicating how the anatomical features look in the pre-operative images of the second imaging modality, include to process the content vector and the style vector through a third neural networks model that is configured to output the estimate of the pre-operative images of the patient in the second imaging modality.

Referring to the example of FIG. 3, the first neural networks model can be a MR encoder neural networks model configured to output a content vector indicating where anatomical features are located in MR pre-operative images. The second neural networks model can be a CT encoder neural networks model configured to output a style vector indicating how the anatomical features look in CT pre-operative images. The third neural networks model can be a CT decoder neural networks model configured to output a synthetic (estimated) CT image or data.

This mechanism allows GNR to generate images with the same content but different appearances. The style component needed for that can be randomly sampled or obtained by encoding an image from the other domain. For some experiments described herein, a style was selected by visually inspecting the sCTs generated using a fixed MR image and styles obtained from CT scans.

Although the first, second, and third neural networks model are described individually, in practice two or more of them may be combined into a single neural networks model. For example, in MR encoder network 1310 and the CT encoder network 1320 may be implemented in a single neural networks model that is trained to perform MR encoding of data input to some of the input nodes and to perform CT encoding of data input to some other input nodes of the neural networks model.

While these operations can work on full 3D scans, they may be computationally expensive for some imaging scenarios. Therefore, in some embodiments the operations only perform 2D image conversion and run the algorithm successively on all slices of the MR volume. Although not explicitly enforce spatial consistency, Chong et al. demonstrates that the network may implicitly learn this property by applying it to subsequent video frames. The following subsections introduce two ideas to further enhance the disentanglement between style and content and harness it to adjust the generated images to a downstream task.

3.2 Content Consistency Loss

Our first experiments with the GNR model showed that the decomposition into style and content had significant benefits but, in some scenarios, may provide deficiencies to be addressed. To emphasize the distinction of content versus style during training, e.g., of the neural networks model, the logic of the GNR approach is extended to encompass the content component as well. We thus devised another set of content-preserving augmentations ac that leave the content of the image unchanged but alter its style: using random gamma corrections, window-level adjustments, and resolution reductions (resizing the image to a smaller size and then back to its original size). This allows us to define a new term, a content consistency loss, that may follow the same rules as the style consistency loss, and be based on the following:

$$L_{cc} = \text{Var}(E_c(B^{aug})), \text{with } B_i^{aug} = a_c(B_j^{tr}), i = 1, \ldots, |B^{tr}|, j \in \{1, |B^{tr}|\} \quad (2)$$

To keep the same memory footprint of the vanilla GNR, we alternate between the style and content consistency loss after each iteration. For example, in one embodiment, training of the neural networks model alternates between a training cycle using the style consistency loss operations to focus training on differences in content between the encoded MR images and encoded CT images, and then another training cycle using the content consistency loss operations to focus training on differences in style between the encoded MR images and encoded CT images.

For example, in some further embodiments, the operations performing training of the first and second neural networks model, where the training alternates between a training cycle using a style consistency loss operation to train based on differences in content between the pre-operative image from the first and second imaging modalities and another training cycle using a content consistency loss operation to train based on differences in style between the pre-operative image from the first and second imaging modalities.

3.3 Optimization of the CT Style

The style component of the GNR network adds flexibility to the model, as it allows to change the appearance of the generated images at inference time without having to change the model's weights (e.g., weights of used by combining nodes in layers of the neural networks model). However, not every style performs equally well when using synthetic images in downstream pipelines. Some embodiments of the present disclosure are directed to fine-tuning the output of the GNR model to different applications. Instead of choosing a style based on aesthetics or by encoding a random target image, some embodiments directly evaluate all (e.g., selected ones of) candidate styles using the GNR model in conjunction with the downstream pipeline. By extension, this allows picking a specific style for each downstream task of interest, since inference is much faster than re-training.

Figure 4:
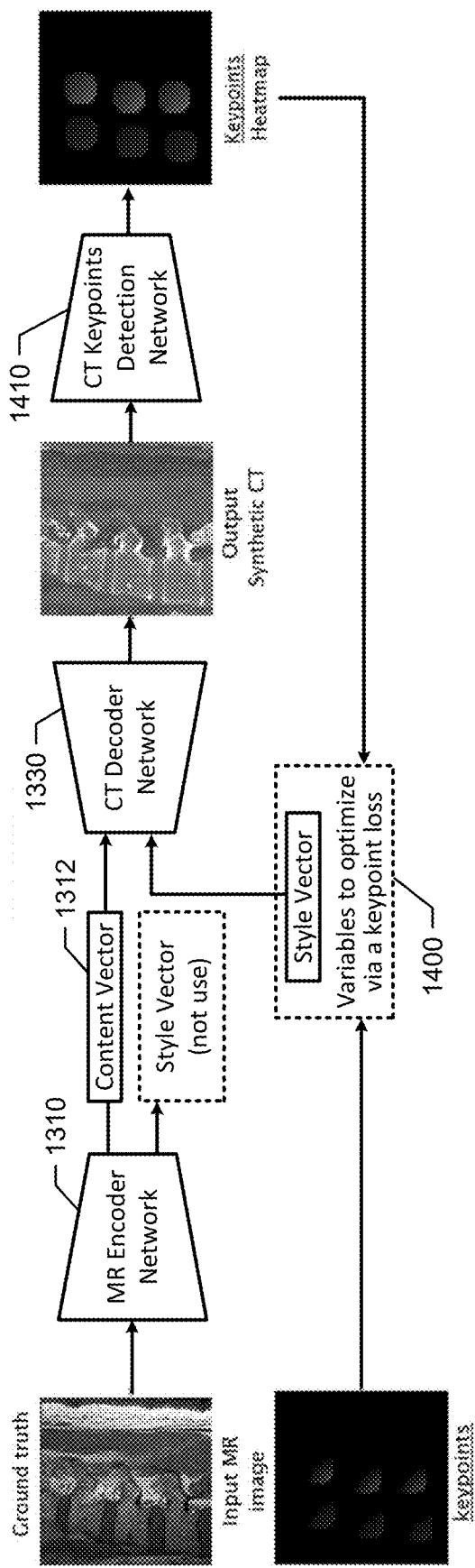
FIG. 4 illustrates a further functional architecture for MR-to-CT modality synthesis that is adapted based on a downstream task in accordance with some embodiments.

In some embodiments, the downstream pipeline includes another neural networks model. In that case, this selection can be made more precise by back-propagating through the target network and the decoder network to directly optimize the style component with gradient descent, such as illustrated in FIG. 4. FIG. 4 illustrates a further functional architecture for MR-to-CT modality synthesis that is adapted based on a downstream task, such as keypoints detection in accordance with some embodiments.

Referring to FIG. 4, an input MR image is encoded through the MR encoder network 1310 to output a content component (content vector) 1312 of the image. Keypoints of the MR image are used by a style generator 1400 to generate a style component (style vector) for the MR detection-based keypoints. The content component (content vector) 1312 and the style component (style vector) 1400 are decoded by the CT decoder network 1330 to output a synthetic CT image, which is processed through a CT keypoints detection network 1410 to output a CT detection-based keypoints heatmap. The CT detection-based keypoints heatmap is fed-back to tune the style generator 1400, e.g., based on comparison of the MR detection-based keypoints and the CT detection-based keypoints.

In some corresponding embodiments, the operations include to process the estimate of the pre-operative images of the patient in the second imaging modality (e.g., synthetic CT in FIGS. 3 and 4) through a fourth neural networks model (e.g., CT keypoints detection network 1410 in FIG. 4) configured to detect keypoints in the pre-operative images of the patient in the second imaging modality (e.g., CT imaging modality). The operations then tune parameters of the second neural networks model (e.g., CT encoder network 1320 in FIG. 3 and/or style component generator 1400 in FIG. 4) based on the detected keypoints in the pre-operative images of the patient in the second imaging modality (e.g., CT imaging modality).

This optimization may be performed using only a handful of samples in accordance with some embodiments. This optimization process may reduce the computational burden and, possibly user burden when a user is involved, for annotation since the fixed and already trained decoder network acts as a form of regularization, reducing the amount of adversarial-image-like high-frequency artifacts in the generated samples.

4. ILLUSTRATIVE EXPERIMENTS

Experiments are now discussed with were performed to investigate two downstream tasks which use pre-existing CT-based algorithms on 3D MR volumes: (i) whole spine keypoints detection and (ii) vertebrae detection and segmentation. In all figures, GNR models with the subscript opt refer to the model with an optimized style component, while the term cc represents training with content consistency regularization.

Approaches according to some embodiments for modality synthesis are compared to two standard baselines for image translation with unpaired data: CycleGAN [18] and CUT [10]. In each case, the code provided by the respective authors and train the models are as outlined in their respective publications.

4.1 Task 1: Vertebra Landmark Detection

The first downstream task tested through a first set of operations is directed to landmark detection. These operations were performed on a scenario in which each vertebra has three keypoints; one for the vertebra's body center and two for left/right pedicles. The operations are based on a simple 3D U-Net with a 3-channel output (one for each keypoint type) that was already trained on publicly available data.

Figure 5A:
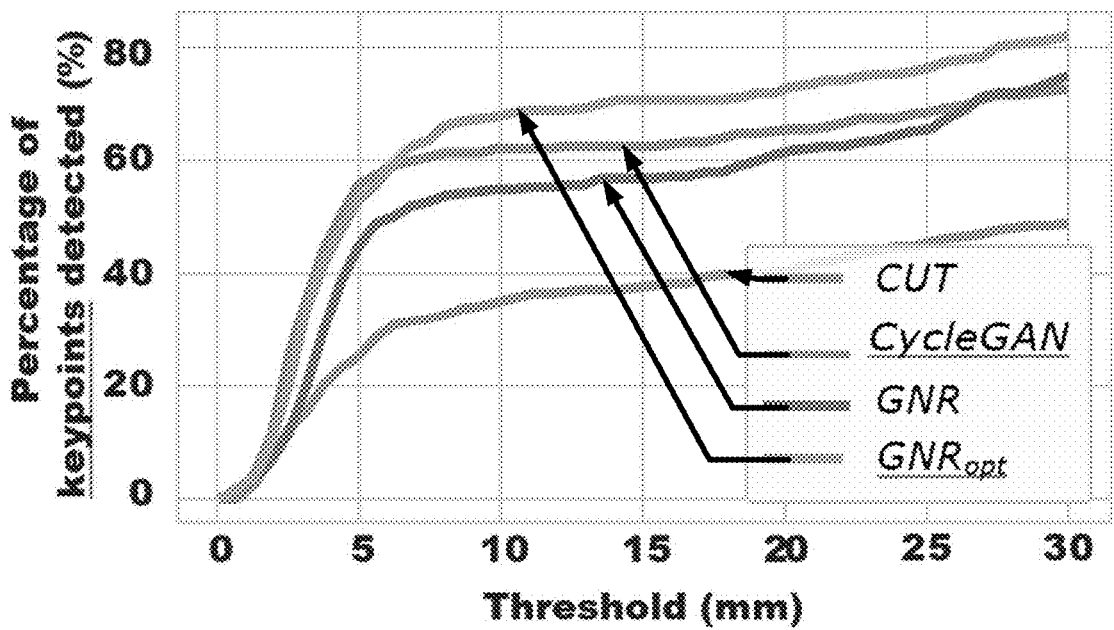
FIG. 5A illustrates a graph of a number of predicted key-points that fall within a given distance from a ground truth point.
Figure 5B:
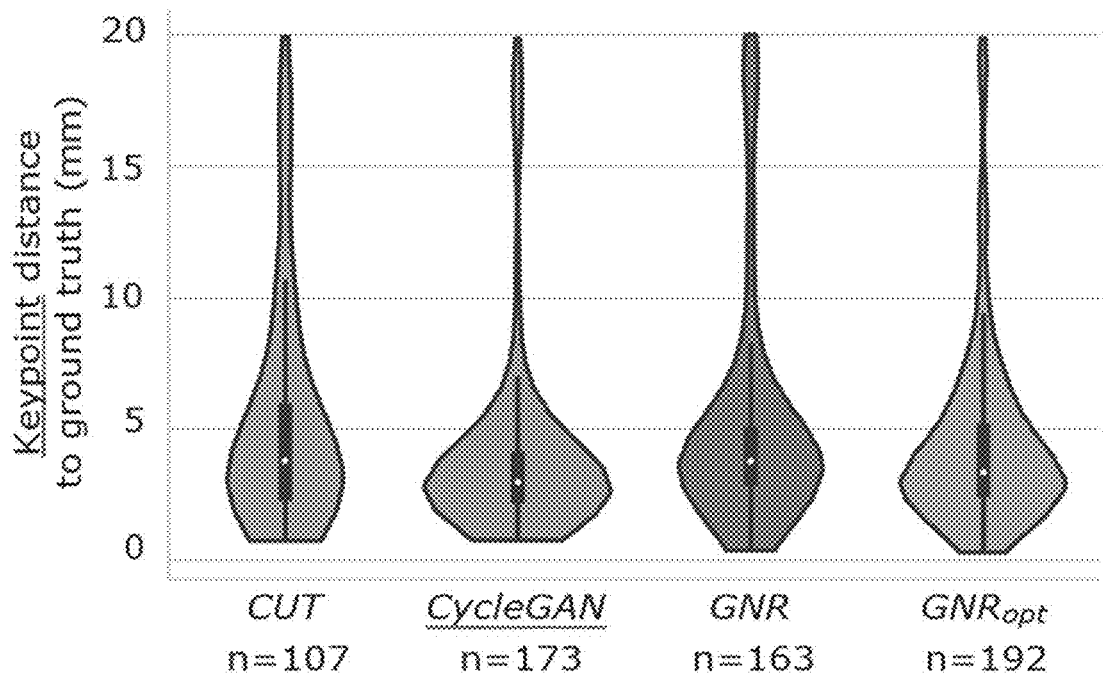
FIG. 5B illustrates a graph of the distribution of distances of matched predicted keypoints within 20 mm of a ground truth keypoint.

Dataset: The operations use an internal dataset of unaligned CT and T1-weighted MRI data from the same patients. The dataset has 14 CT volumes with 25 MRI volumes, 18 of which have landmark annotations, and includes partial and full spine scans. Splitting the volumes into sagittal slices resulted in 412 MRI and 2713 CT images. The operations resampled these 2D images to 0.5 mm and 0.75 mm resolutions and sampled randomly placed 256×256 ROIs at each resolution. To even out the CT to MR data imbalance, the operations sampled three ROIs from each MRI image. FIGS. 5A and 5B illustrate example results of the keypoint prediction on synthetic CT images (sCTs). FIG. 5A illustrates a graph of a number of predicted key-points that fall within a given distance from a ground truth point. FIG. 5B illustrates a graph of the distribution of distances of matched predicted keypoints within 20 mm of a ground truth keypoint.

Style Optimization: The operations reserved 8 MR volumes to test the proposed style optimization; 4 for training and 4 for validation. As the keypoint model expects 3D inputs, the operations cropped a 256×256×N (with N being the number of slices in each volume) portion of the volume where the spine is visible and converted each slice in the crop separately. The mean squared error between the model's prediction and the ground truth keypoints encoded as 3-channel Gaussian blobs served as the supervisory signal for optimizing the style. The operations used the Adam optimizer and stopped after 20 iterations with no improvement in the validation loss. The optimization took on the order of 10 minutes to complete.

Results: The sCTs were evaluated using the 8 MRI volumes not considered in the style optimization. To create a matching between predicted and ground truth keypoints, the operations calculated the Euclidian distance from every ground truth point to each predicted one and selected the point with the minimal distance as a matching candidate. FIG. 5A shows the distribution of distances per model after applying a 20 mm cutoff, which is on the order of the average vertebral body height [6]. The graph of FIG. 5B shows how the proportion of detected keypoints changes with this threshold.

Out of the four methods (CUT, CycleGAN, GNR, GNRopt), the optimized GNR model (GRNopt) yields the most keypoints, while the CUT model shows the worst performance. In particular, we observe the benefit of optimizing the style vector of the GNR over picking a visually pleasing style. The comparison with CycleGAN is more nuanced: CycleGAN results in slightly more accurate keypoints at the cost of fewer (about 11%) matches. CycleGAN's low consistency in generating images may explain this: some sCTs seem more accurate, while in others, fictitious soft tissue takes the place of the spine. Given the slight absolute difference in accuracy, we believe the trade-off favors GNRs.

4.2 Task 2: Semantic Vertebra Segmentation:

A second set of example operations are directed to a full spine analysis, encompassing classification and segmentation of each vertebra, using the commercial software ImFusion Suite (ImFusion GmbH, Germany). As this is a closed algorithm, the operations do not optimize the style directly since there is no access to the gradients. Instead, the operations are based on the methodology from 4.1, relying on the same or similar pre-trained keypoint model, to investigate whether it generalizes to a related application. To this end, the operations, e.g., which may be performed manually, annotated keypoints in 8 MRI volumes of the MRSpineSeg dataset (4 each for training and validation).

Dataset: The operations use two public and independent datasets. For the MR domain, the operations were based on the MRSpineSeg dataset [9] which encompasses 172 T2-weighted sagittal MR volumes. The images show up to 9 vertebrae (L5-T19) and include manual segmentations. For the CT domain, the operations used 88 spine CT volumes from the Verse challenge [11]. After splitting the volumes sagittally and resizing the slices to 256×256, the resulting set was 5680 CT and 2172 MR slices.

Evaluation: To obtain the vertebra segmentations and classifications, the operations first constructed sCTs by converting the MRI volumes slice-wise using the trained synthesis models and creating label maps by then running the commercial algorithm. Afterwards, the operations computed the Dice between each label in the ground truth and prediction and kept the one with the highest score as a matching candidate. The operations then discarded all candidates that have a Dice score of less than 0.5 to the ground truth label they matched with.

Results: The hierarchy of the methods is unchanged: The CUT model misses a lot of vertebrae, while GNR models detect most of them (the best model achieves a median of 100% of vertebrae detection). The CycleGAN is again slightly more accurate in terms of segmentation on the subset of detected vertebrae but is inconsistent in detecting them in the first place. Furthermore, the confusion matrices indicate a much higher classification accuracy for the proposed GNR model (F1-score of 0.724 vs. 0.334). Finally, we again observe the effect of both our contributions: the models with content consistency and optimized style are superior in all metrics compared to the vanilla GNR (p-value<0.01 with a Mann-Whitney-U test for the Dice and Wilcoxon signed-rank test for the fraction of detected vertebrae).

Figure 6:
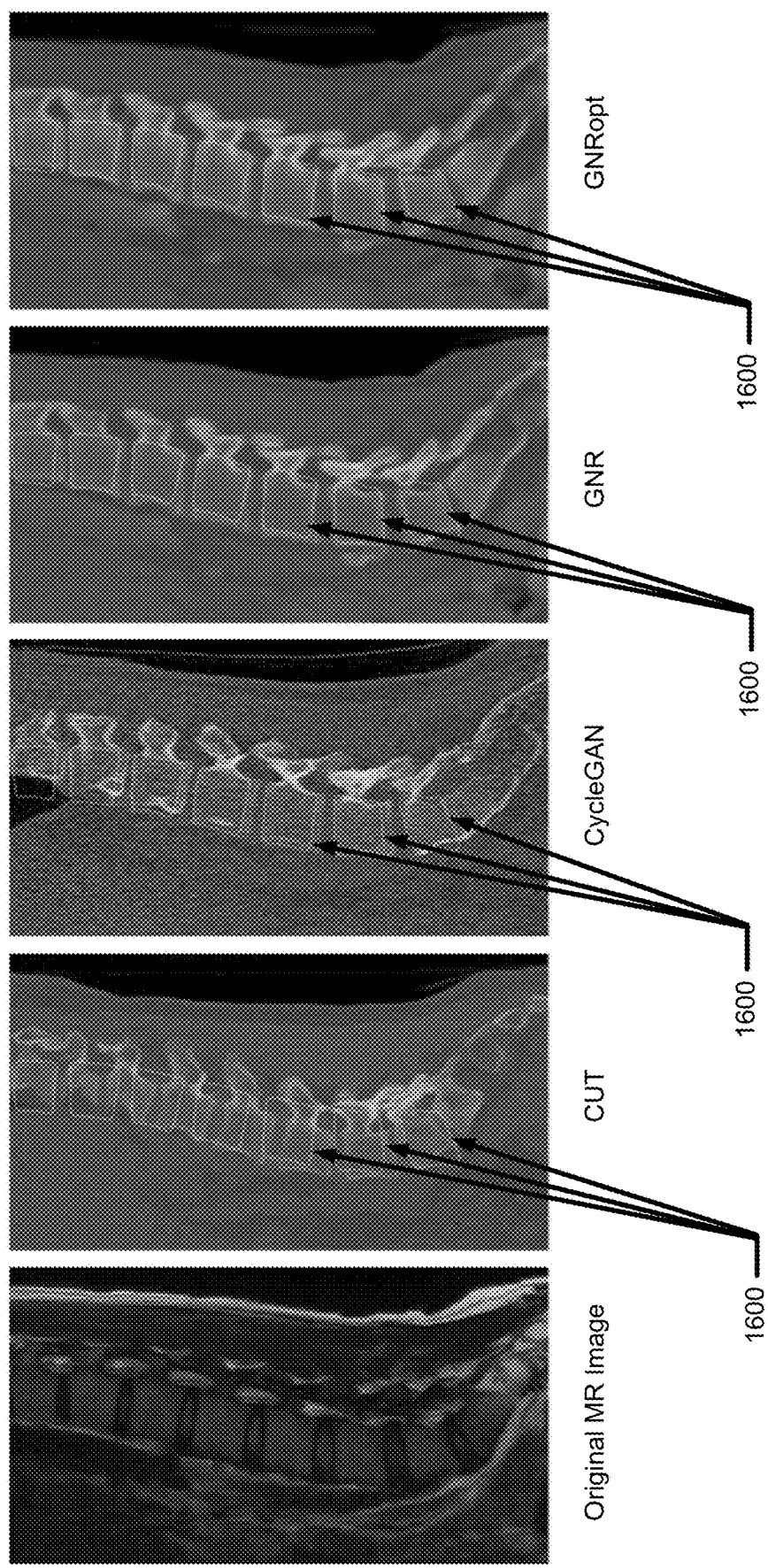
FIG. 6 illustrates a visual comparison of the generated images for the median case.

FIG. 6 illustrates a visual comparison of the generated images for the median case (with respect to Dice). Graphical overlays 1600 indicate the vertebra body outlines by each of the models. The CUT model can generate plausible images but has the same inconsistency problem as the CycleGAN. Additionally, it does not preserve the original content. CycleGAN does a better job regarding preservation of content but overwhelmingly generates noisy images without the possibility of adjustment. The difference between GNRcc and GNRcc,opt images is more subtle but present: the latter provides images where the vertebrae bodies have higher intensities and therefore a better contrast to the background.

Figure 7A:
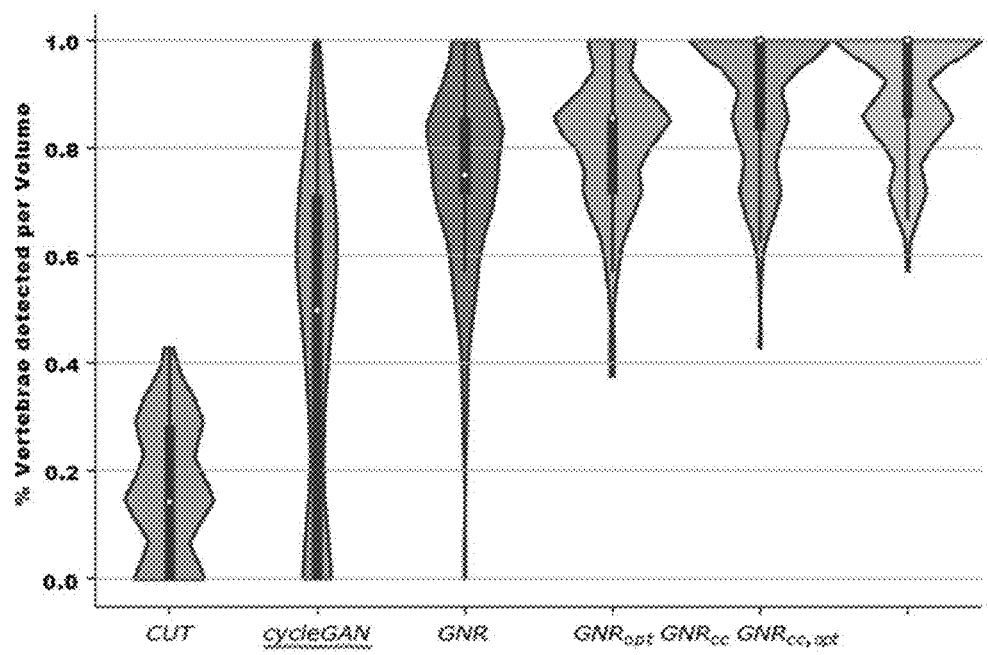
FIG. 7A illustrates distributions of the fraction of detected vertebrae.
Figure 7B:
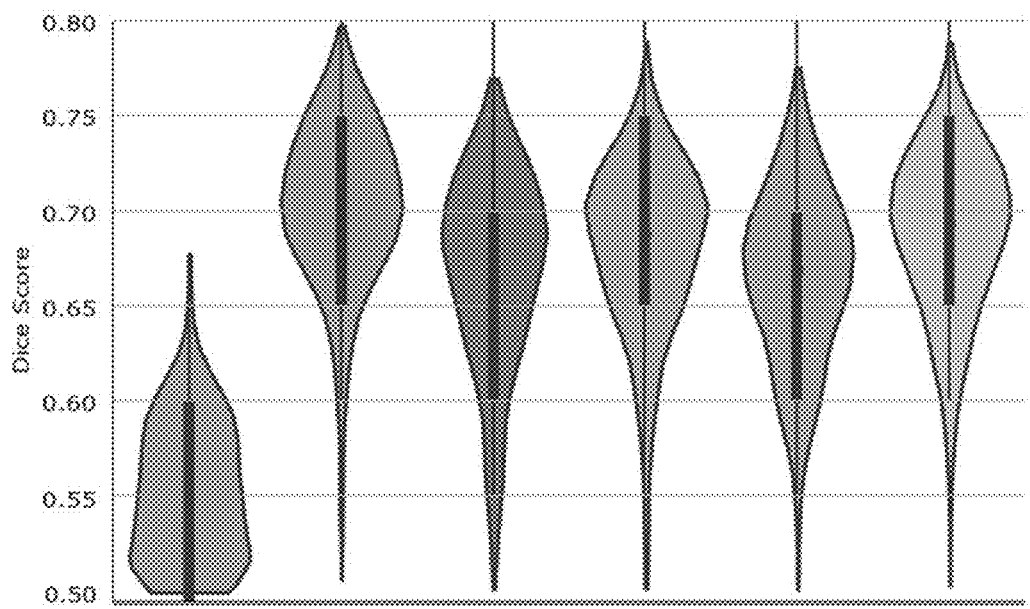
FIG. 7B illustrates distributions of the measured dice.
Figure 7C:
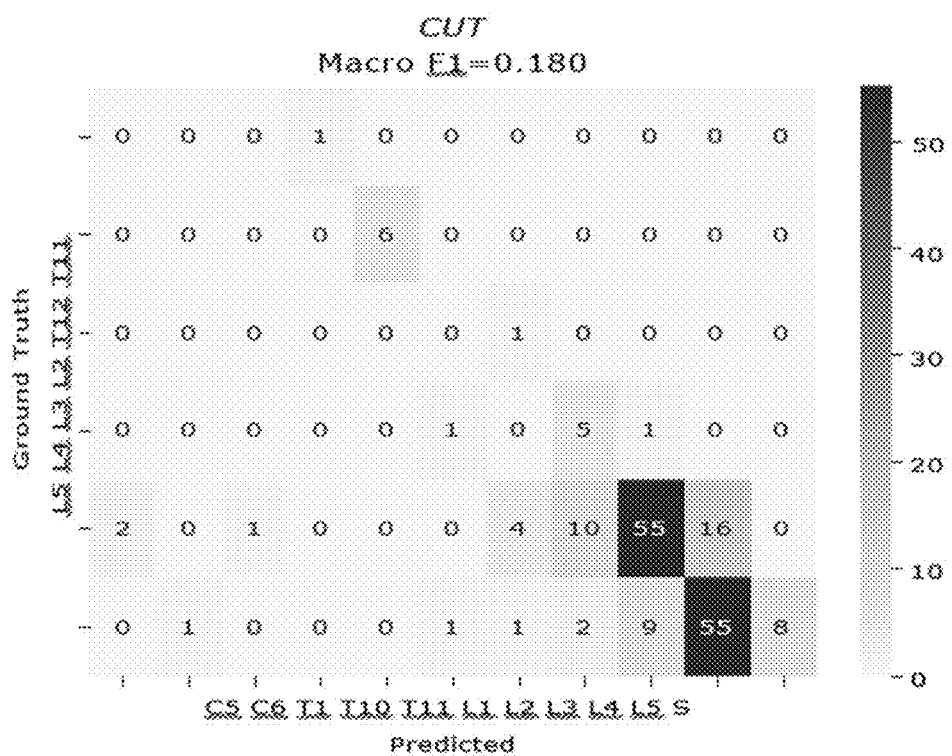
FIG. 7C illustrates confusion matrices for the detected subset from CUT.
Figure 7D:
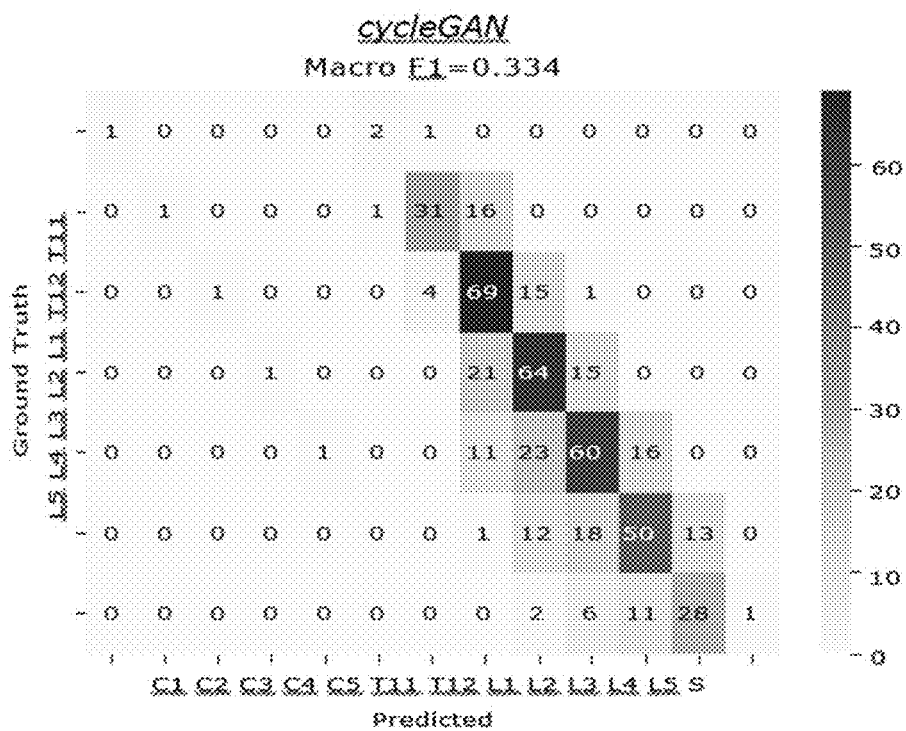
FIG. 7D illustrates confusion matrices for the detected subset from cycleGAN.
Figure 7E:
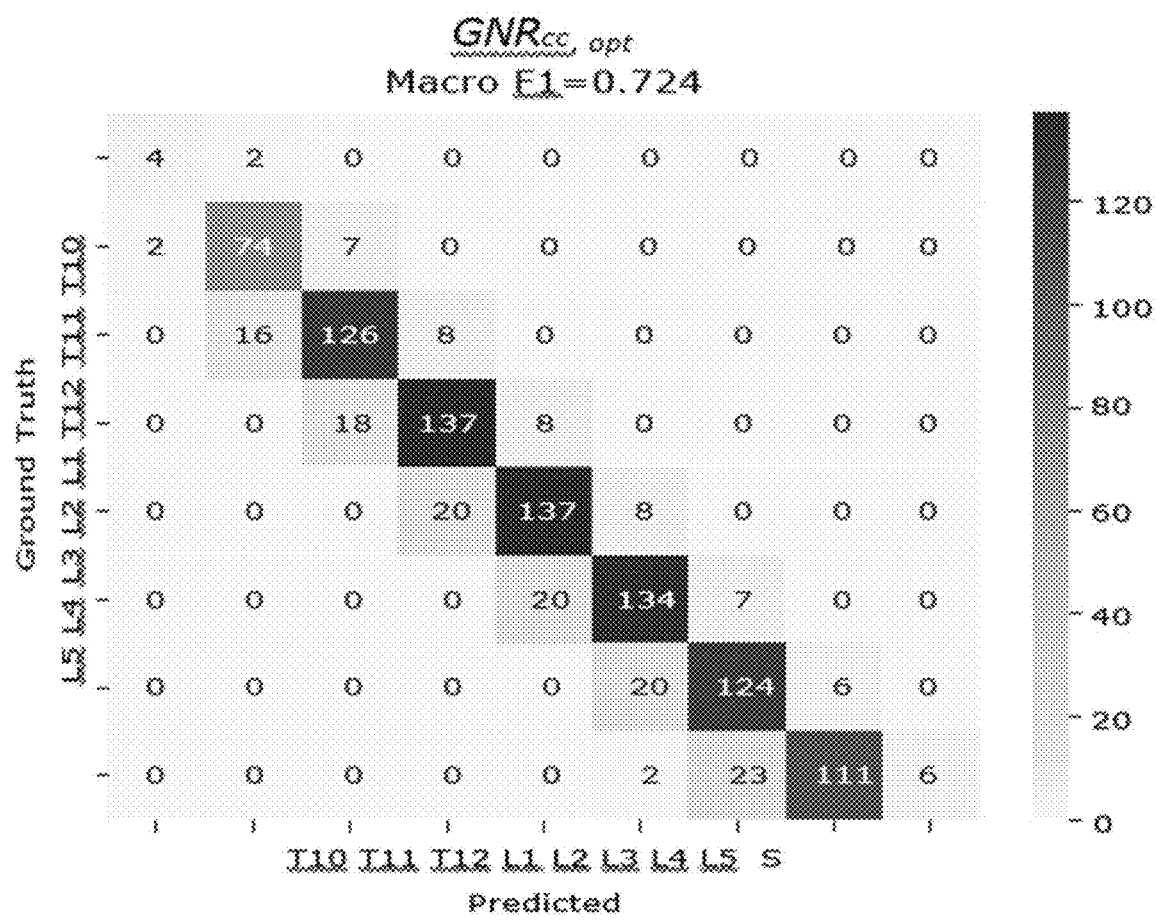
FIG. 7E illustrates confusion matrices for the detected subset from GNR and GRNopt.

FIGS. 7A, 7B, 7C, 7D, and 7E illustrate results of the semantic segmentation on sCTs. FIG. 7A illustrates distributions of the fraction of detected vertebrae. FIG. 7B illustrates distributions of the measured dice. FIG. 7C illustrates confusion matrices for the detected subset from CUT. FIG. 7D illustrates confusion matrices for the detected subset from cycleGAN. FIG. 7E illustrates confusion matrices for the detected subset from GNR and GRNopt.

5. POTENTIAL BENEFITS OF VARIOUS EMBODIMENTS

Various embodiments have been discussed which are directed to methods and corresponding operations for generating synthetic CT volumes from MR scans that can be trained without paired or registered data. Some embodiments are partially based upon the Gans'N'Roses algorithm but extending it via a content consistency loss and an automated adaptation of the style vector to a target task. Some embodiments have been demonstrated on two different applications that the separation between anatomy and appearance positively impacts performance in downstream pipelines. One observation from this work is that the most visually pleasing styles are not necessarily best suited when subjecting sCTs to further processing. Optimizing the style of the generator may provide valuable insights into what the subsequent models look for in their inputs.

The disentanglement of style and content provided by GNR models can provide operational benefits. For instance, interpolation in the content space could form a method for out-of-plane image super-resolution.

6. Example Navigated Surgical System and Operations According to Some Further Embodiments Further embodiments are now described which are directed to using one or more of the embodiments discussed above in a navigated surgery system. These further embodiments are described with reference to FIGS. 8 through 11.

Figure 8:
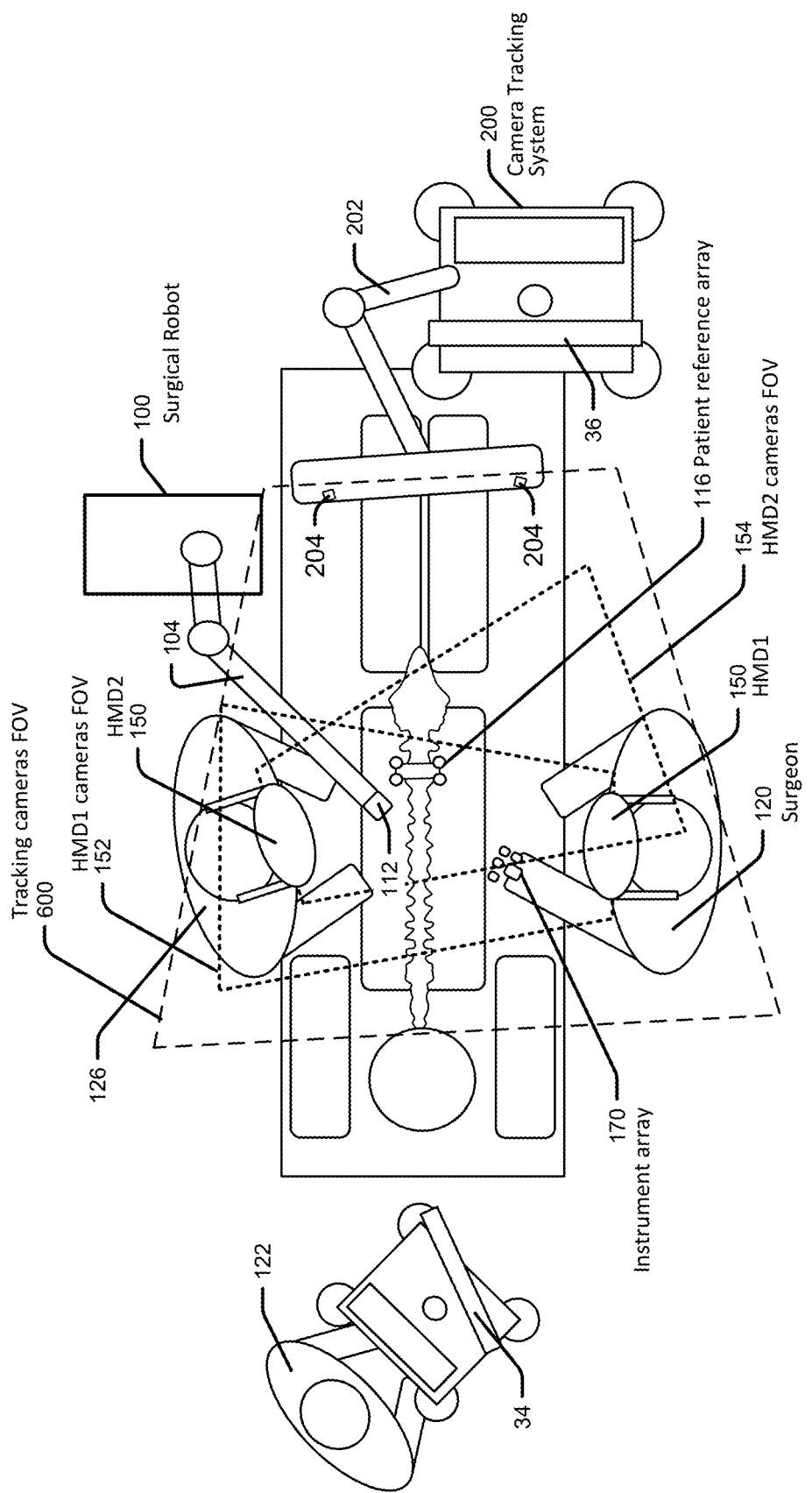
FIG. 8 illustrates an overhead view of a surgical system arranged during a surgical procedure in a surgical room which includes a camera tracking system for navigated surgery and which may further include a surgical robot for robotic assistance according to some embodiments.
Figure 9:
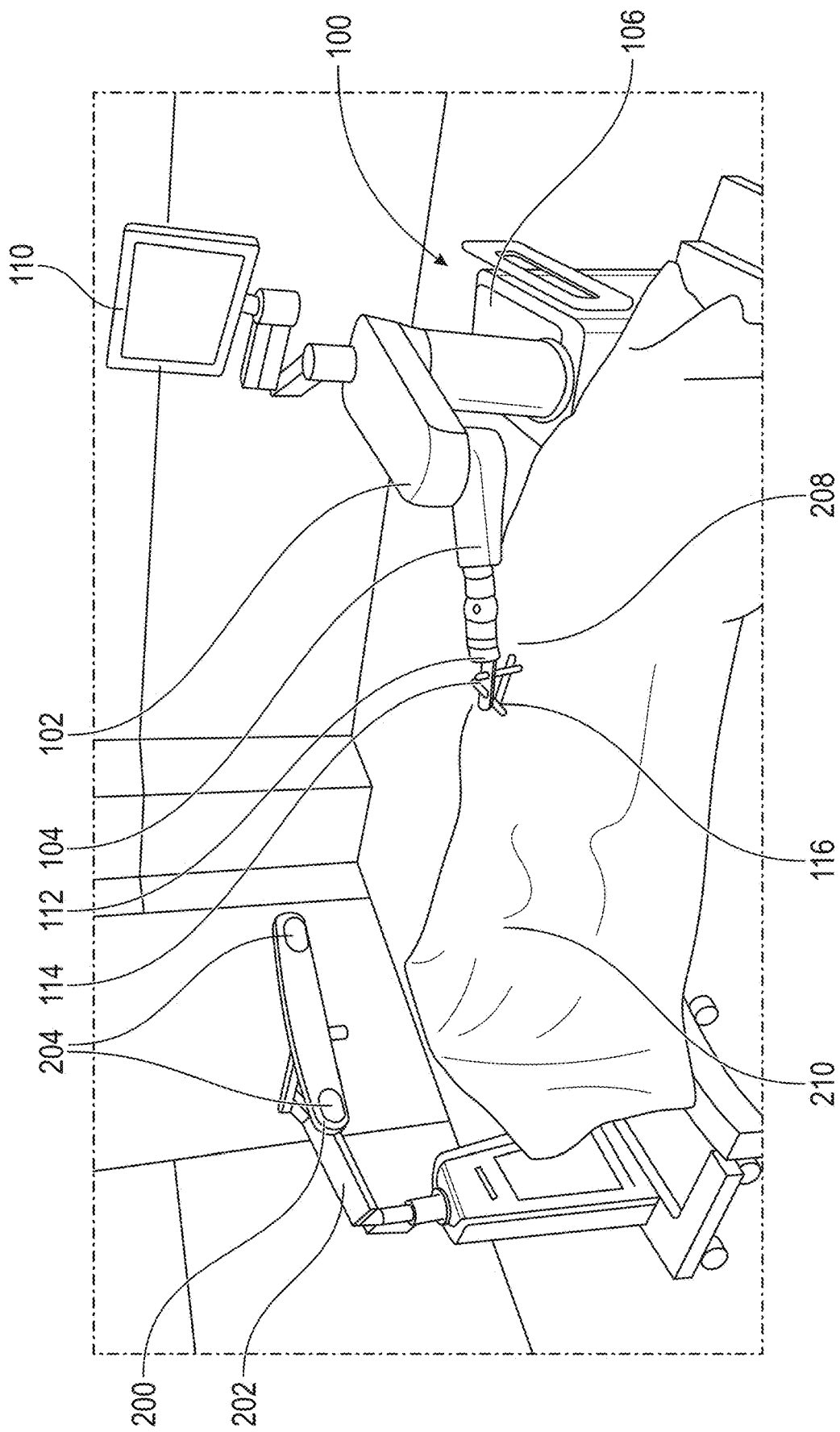
FIG. 9 illustrates the camera tracking system and the surgical robot positioned relative to a patient according to some embodiments.
Figure 10:
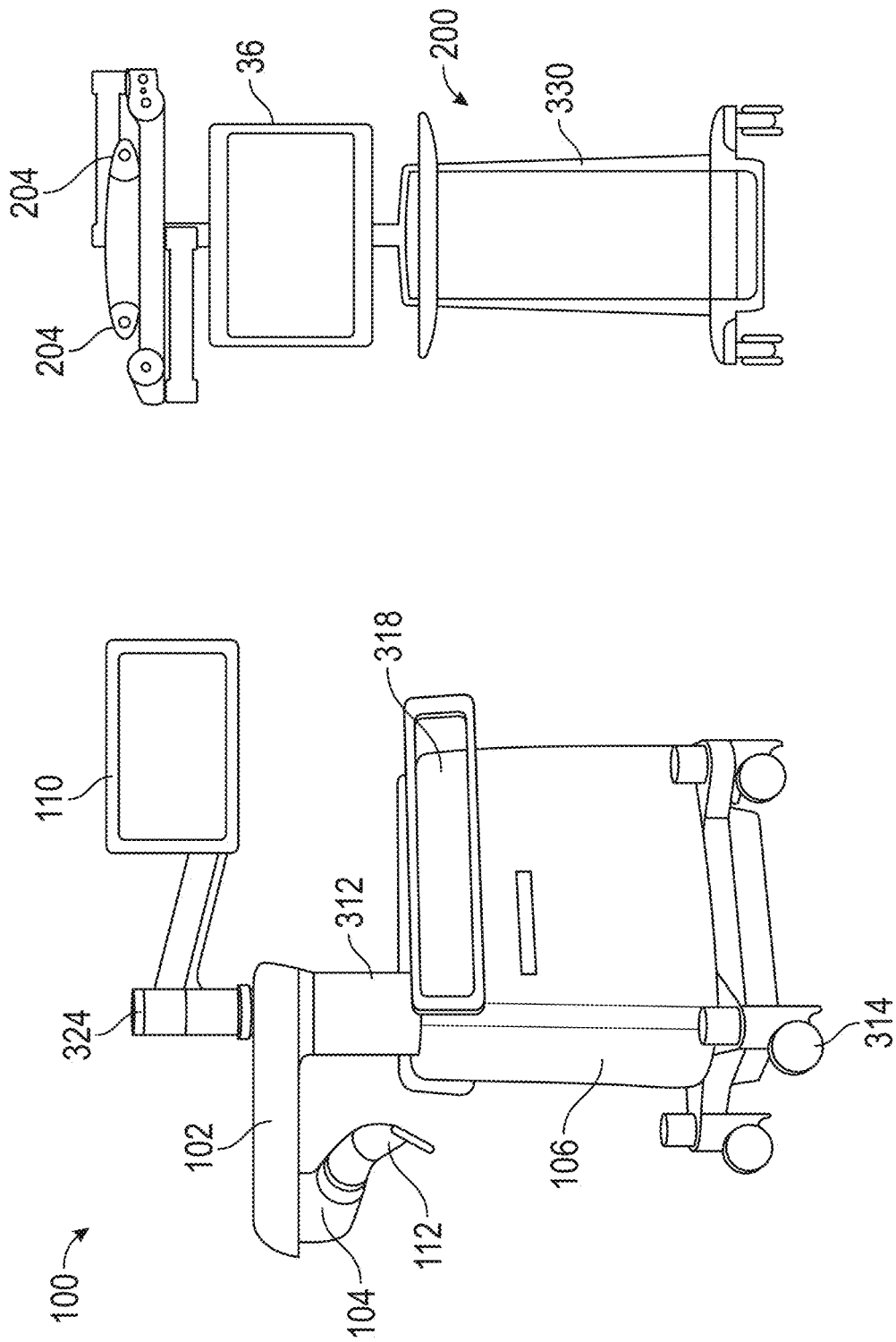
FIG. 10 further illustrates the camera tracking system and the surgical robot configured according to some embodiments.
Figure 11:
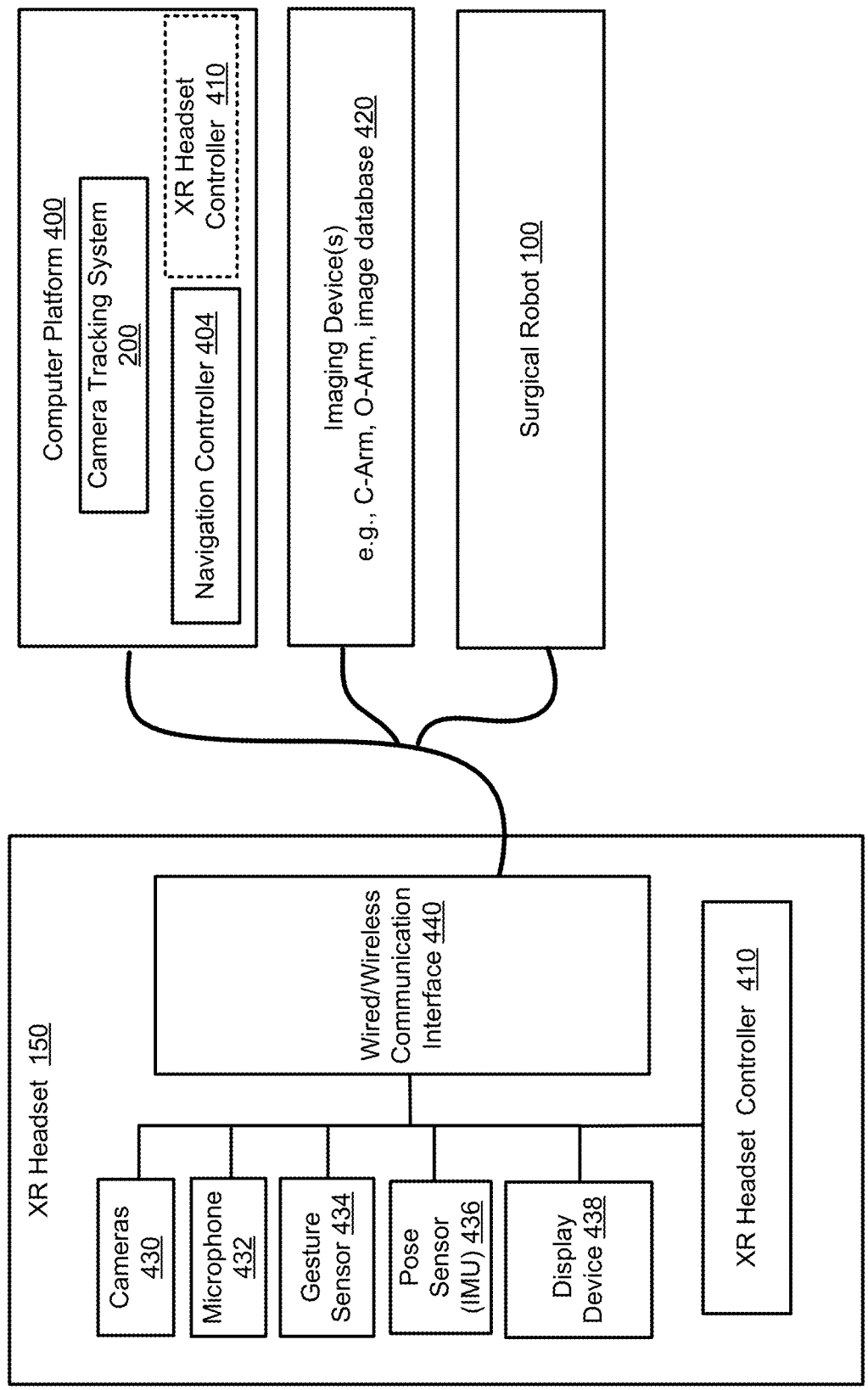
FIG. 11 illustrates a block diagram of a surgical system that includes an XR headset, a computer platform, imaging devices, and a surgical robot which are configured to operate according to some embodiments.

FIG. 8 is an overhead view of a surgical system arranged during a surgical procedure in a surgical room which includes a camera tracking system 200 for navigated surgery and which may further include a surgical robot 100 for robotic assistance according to some embodiments. FIG. 9 illustrates the camera tracking system 200 and the surgical robot 100 positioned relative to a patient according to some embodiments. FIG. 10 further illustrates the camera tracking system 200 and the surgical robot 100 configured according to some embodiments. FIG. 11 illustrates a block diagram of a surgical system that includes an XR headset 150, a computer platform 400, imaging devices 420, and the surgical robot 100 which are configured to operate according to some embodiments.

The XR headsets 150 may be configured to augment a real-world scene with computer generated XR images while worn by personnel in the operating room. The XR headsets 150 may be configured to provide an augmented reality (AR) viewing environment by displaying the computer generated XR images on a see-through display screen that allows light from the real-world scene to pass therethrough for combined viewing by the user. Alternatively, the XR headsets 150 may be configured to provide a virtual reality (VR) viewing environment by preventing or substantially preventing light from the real-world scene from being directly viewed by the user while the user is viewing the computer-generated AR images on a display screen. The XR headsets 150 can be configured to provide both AR and VR viewing environments. Thus, the term XR headset can referred to as an AR headset or a VR headset.

Referring to FIG. 8 through 11, the surgical robot 100 may include, for example, one or more robot arms 104, a display 110, an end-effector 112, for example, including a guide tube 114, and an end effector reference array which can include one or more tracking markers. A patient reference array 116 (DRB) has a plurality of tracking markers 117 and is secured directly to the patient 210 (e.g., to a bone of the patient 210). A reference array 170 is attached or formed on an instrument, surgical tool, surgical implant device, etc.

The camera tracking system 200 includes tracking cameras 204 which may be spaced apart stereo cameras configured with partially overlapping field-of-views. The camera tracking system 200 can have any suitable configuration of arm(s) 202 to move, orient, and support the tracking cameras 204 in a desired location, and may contain at least one processor operable to track location of an individual marker and pose of an array of markers.

As used herein, the term "pose" refers to the location (e.g., along 3 orthogonal axes) and/or the rotation angle (e.g., about the 3 orthogonal axes) of markers (e.g., DRB) relative to another marker (e.g., surveillance marker) and/or to a defined coordinate system (e.g., camera coordinate system). A pose may therefore be defined based on only the multidimensional location of the markers relative to another marker and/or relative to the defined coordinate system, based on only the multidimensional rotational angles of the markers relative to the other marker and/or to the defined coordinate system, or based on a combination of the multidimensional location and the multidimensional rotational angles. The term "pose" therefore is used to refer to location, rotational angle, or combination thereof.

The tracking cameras 204 may include, e.g., infrared cameras (e.g., bifocal or stereophotogrammetric cameras), operable to identify, for example, active and passive tracking markers for single markers (e.g., surveillance marker) and reference arrays which can be formed on or attached to the patient 210 (e.g., patient reference array, DRB), end effector 112 (e.g., end effector reference array), XR headset(s) 150 worn by a surgeon 120 and/or a surgical assistant 126, etc. in a given measurement volume of a camera coordinate system while viewable from the perspective of the tracking cameras 204. The tracking cameras 204 may scan the given measurement volume and detect light that is emitted or reflected from the markers in order to identify and determine locations of individual markers and poses of the reference arrays in three-dimensions. For example, active reference arrays may include infrared-emitting markers that are activated by an electrical signal (e.g., infrared light emitting diodes (LEDs)), and passive reference arrays may include retro-reflective markers that reflect infrared light (e.g., they reflect incoming IR radiation into the direction of the incoming light), for example, emitted by illuminators on the tracking cameras 204 or other suitable device.

The XR headsets 150 may each include tracking cameras (e.g., spaced apart stereo cameras) that can track location of a surveillance marker and poses of reference arrays within the XR camera headset field-of-views (FOVs) 152 and 154, respectively. Accordingly, as illustrated in FIG. 1, the location of the surveillance marker and the poses of reference arrays on various objects can be tracked while in the FOVs 152 and 154 of the XR headsets 150 and/or a FOV 600 of the tracking cameras 204.

FIGS. 8 and 9 illustrate a potential configuration for the placement of the camera tracking system 200 and the surgical robot 100 in an operating room environment. Computer-aided navigated surgery can be provided by the camera tracking system controlling the XR headsets 150 and/or other displays 34, 36, and 110 to display surgical procedure navigation information. The surgical robot 100 is optional during computer-aided navigated surgery.

The camera tracking system 200 may operate using tracking information and other information provided by multiple XR headsets 150 such as inertial tracking information and optical tracking information (frames of tracking data). The XR headsets 150 operate to display visual information and may play-out audio information to the wearer. This information can be from local sources (e.g., the surgical robot 100 and/or other medical), remote sources (e.g., patient medical image server), and/or other electronic equipment. The camera tracking system 200 may track markers in 6 degrees-of-freedom (6 DOF) relative to three axes of a 3D coordinate system and rotational angles about each axis. The XR headsets 150 may also operate to track hand poses and gestures to enable gesture-based interactions with "virtual"

buttons and interfaces displayed through the XR headsets 150 and can also interpret hand or finger pointing or gesturing as various defined commands. Additionally, the XR headsets 150 may have a 1-10× magnification digital color camera sensor called a digital loupe. In some embodiments, one or more of the XR headsets 150 are minimalistic XR headsets that display local or remote information but include fewer sensors and are therefore more lightweight.

An "outside-in" machine vision navigation bar supports the tracking cameras 204 and may include a color camera. The machine vision navigation bar generally has a more stable view of the environment because it does not move as often or as quickly as the XR headsets 150 while positioned on wearers' heads. The patient reference array 116 (DRB) is generally rigidly attached to the patient with stable pitch and roll relative to gravity. This local rigid patient reference 116 can serve as a common reference for reference frames relative to other tracked arrays, such as a reference array on the end effector 112, instrument reference array 170, and reference arrays on the XR headsets 150.

During a surgical procedure using surgical navigation, a surveillance marker can be affixed to the patient to provide information on whether the patient reference array 116 has shifted. For example, during a spinal fusion procedure with planned placement of pedicle screw fixation, two small incisions are made over the posterior superior iliac spine bilaterally. The DRB and the surveillance marker are then affixed to the posterior superior iliac spine bilaterally.

When present, the surgical robot (also "robot") may be positioned near or next to patient 210. The robot 100 can be positioned at any suitable location near the patient 210 depending on the area of the patient 210 undergoing the surgical procedure. The camera tracking system 200 may be separated from the robot system 100 and positioned at the foot of patient 210. This location allows the tracking camera 200 to have a direct visual line of sight to the surgical area 208. In the configuration shown, the surgeon 120 may be positioned across from the robot 100, but is still able to manipulate the end-effector 112 and the display 110. A surgical assistant 126 may be positioned across from the surgeon 120 again with access to both the end-effector 112 and the display 110. If desired, the locations of the surgeon 120 and the assistant 126 may be reversed. An anesthesiologist 122, nurse or scrub tech can operate equipment which may be connected to display information from the camera tracking system 200 on a display 34.

With respect to the other components of the robot 100, the display 110 can be attached to the surgical robot 100 or in a remote location. End-effector 112 may be coupled to the robot arm 104 and controlled by at least one motor. In some embodiments, end-effector 112 can comprise a guide tube 114, which is configured to receive and orient a surgical instrument, tool, or implant used to perform a surgical procedure on the patient 210.

As used herein, the term "end-effector" is used interchangeably with the terms "end-effectuator" and "effectuator element." The term "instrument" is used in a non-limiting manner and can be used interchangeably with "tool" and "implant" to generally refer to any type of device that can be used during a surgical procedure in accordance with embodiments disclosed herein. The more general term device can also refer to structure of the end-effector, etc. Example instruments, tools, and implants include, without limitation, drills, screwdrivers, saws, dilators, retractors, probes, implant inserters, and implant devices such as a screws, spacers, interbody fusion devices, plates, rods, etc. Although generally shown with a guide tube 114, it will be appreciated that the end-effector 112 may be replaced with any suitable instrumentation suitable for use in surgery. In some embodiments, end-effector 112 can comprise any known structure for effecting the movement of the surgical instrument in a desired manner.

The surgical robot 100 is operable to control the translation and orientation of the end-effector 112. The robot 100 may move the end-effector 112 under computer control along x-, y-, and z-axes, for example. The end-effector 112 can be configured for selective rotation about one or more of the x-, y-, and z-axis, and a Z Frame axis, such that one or more of the Euler Angles (e.g., roll, pitch, and/or yaw) associated with end-effector 112 can be selectively computer controlled. In some embodiments, selective control of the translation and orientation of end-effector 112 can permit performance of medical procedures with significantly improved accuracy compared to conventional robots that utilize, for example, a 6 DOF robot arm comprising only rotational axes. For example, the surgical robot 100 may be used to operate on patient 210, and robot arm 104 can be positioned above the body of patient 210, with end-effector 112 selectively angled relative to the z-axis toward the body of patient 210.

In some example embodiments, the XR headsets 150 can be controlled to dynamically display an updated graphical indication of the pose of the surgical instrument so that the user can be aware of the pose of the surgical instrument at all times during the procedure.

In some further embodiments, surgical robot 100 can be operable to correct the path of a surgical instrument guided by the robot arm 104 if the surgical instrument strays from the selected, preplanned trajectory. The surgical robot 100 can be operable to permit stoppage, modification, and/or manual control of the movement of end-effector 112 and/or the surgical instrument. Thus, in use, a surgeon or other user can use the surgical robot 100 as part of computer assisted navigated surgery, and has the option to stop, modify, or manually control the autonomous or semi-autonomous movement of the end-effector 112 and/or the surgical instrument.

Reference arrays of markers can be formed on or connected to robot arms 102 and/or 104, the end-effector 112 (e.g., end-effector array 114 in FIG. 2), and/or a surgical instrument (e.g., instrument array 170) to track poses in 6 DOF along 3 orthogonal axes and rotation about the axes. The reference arrays enable each of the marked objects (e.g., the end-effector 112, the patient 210, and the surgical instruments) to be tracked by the tracking camera 200, and the tracked poses can be used to provide navigated guidance during a surgical procedure and/or used to control movement of the surgical robot 100 for guiding the end-effector 112 and/or an instrument manipulated by the end-effector 112.

Although not illustrated in FIGS. 8 and 9, various medical imaging devices can be used to obtain intra-operative images or data of a patient in various different imaging modalities. For example, a C-arm or O-arm CT imaging device can be used to obtain intra-operative CT images of a patient. An X-ray and/or fluoroscopy device can be used to obtain intra-operative x-ray images. An ultrasound imaging device can be used to obtain intra-operative ultrasound images. An MRI device can be used to obtain intra-operative MRI images. These imaging devices can be include optical markers, x-ray opaque markers (fiducials), or other mechanisms to enable registration of the images or data output by the imaging devices to a coordinate system tracked by the camera tracking system 200, in order to provide navigable images which can be used to provide computer assisted navigation during a surgical procedure on the patient.

Referring to FIG. 3 the surgical robot 100 may include a display 110, upper arm 102, lower arm 104, end-effector 112, vertical column 312, casters 314, a table 318, and ring 324 which uses lights to indicate statuses and other information. Cabinet 106 may house electrical components of surgical robot 100 including, but not limited, to a battery, a power distribution module, a platform interface board module, and a computer. The camera tracking system 200 may include a display 36, tracking cameras 204, arm(s) 202, a computer housed in cabinet 330, and other components.

In computer-assisted navigated surgeries, perpendicular 2D scan slices, such as axial, sagittal, and/or coronal views, of patient anatomical structure are displayed to enable user visualization of the patient's anatomy alongside the relative poses of surgical instruments. An XR headset or other display can be controlled to display one or more 2D scan slices of patient anatomy along with a 3D graphical model of anatomy. The 3D graphical model may be generated from a 3D scan of the patient, e.g., by a CT scan device, and/or may be generated based on a baseline model of anatomy which isn't necessarily formed from a scan of the patient.

Example Surgical System

FIG. 11 illustrates a block diagram of a surgical system that includes an XR headset 150, a computer platform 400, imaging devices 420 (e.g., MRI, CT, ultrasound, etc.), and a surgical robot 100 which are configured to operate according to some embodiments.

The imaging devices 420 may include a C-arm imaging device, an O-arm imaging device, ultrasound imaging device, and/or a patient image database. The XR headset 150 provides an improved human interface for performing navigated surgical procedures. The XR headset 150 can be configured to provide functionalities, e.g., via the computer platform 400, that include without limitation any one or more of: identification of hand gesture based commands, display XR graphical objects on a display device 438 of the XR headset 150 and/or another display device. The display device 438 may include a video projector, flat panel display, etc. The user may view the XR graphical objects as an overlay anchored to particular real-world objects viewed through a see-through display screen. The XR headset 150 may additionally or alternatively be configured to display on the display device 438 video streams from cameras mounted to one or more XR headsets 150 and other cameras.

Electrical components of the XR headset 150 can include a plurality of cameras 430, a microphone 432, a gesture sensor 434, a pose sensor (e.g., inertial measurement unit (IMU)) 436, the display device 438, and a wireless/wired communication interface 440. The cameras 430 of the XR headset 150 may be visible light capturing cameras, near infrared capturing cameras, or a combination of both.

The cameras 430 may be configured to operate as the gesture sensor 434 by tracking for identification user hand gestures performed within the field-of-view of the camera(s) 430. Alternatively, the gesture sensor 434 may be a proximity sensor and/or a touch sensor that senses hand gestures performed proximately to the gesture sensor 434 and/or senses physical contact, e.g., tapping on the sensor 434 or its enclosure. The pose sensor 436, e.g., IMU, may include a multi-axis accelerometer, a tilt sensor, and/or another sensor that can sense rotation and/or acceleration of the XR headset 150 along one or more defined coordinate axes. Some or all of these electrical components may be contained in a head-worn component enclosure or may be contained in another enclosure configured to be worn elsewhere, such as on the hip or shoulder.

As explained above, the surgical system includes the camera tracking system 200 which may be connected to a computer platform 400 for operational processing and which may provide other operational functionality including a navigation controller 404 and/or of an XR headset controller 410. The computer platform 400 can be configured according to one or more embodiments disclosed herein to register pre-operative images of the patient to intra-operative navigable images or data of the patient. The surgical system may include the surgical robot 100. The navigation controller 404 can be configured to provide visual navigation guidance to an operator for moving and positioning a surgical tool relative to patient anatomical structure based on a surgical plan, e.g., from a surgical planning function, defining where a surgical procedure is to be performed using the surgical tool on the anatomical structure and based on a pose of the anatomical structure determined by the camera tracking system 200. The navigation controller 404 may be further configured to generate navigation information based on a target pose for a surgical tool, a pose of the anatomical structure, and a pose of the surgical tool and/or an end effector of the surgical robot 100, where the steering information is displayed through the display device 438 of the XR headset 150 and/or another display device to indicate where the surgical tool and/or the end effector of the surgical robot 100 should be moved to perform the surgical plan.

The electrical components of the XR headset 150 can be operatively connected to the electrical components of the computer platform 400 through the wired/wireless interface 440. The electrical components of the XR headset 150 may be operatively connected, e.g., through the computer platform 400 or directly connected, to various imaging devices 420, e.g., the C-arm imaging device, the I/O-arm imaging device, the patient image database, and/or to other medical equipment through the wired/wireless interface 440.

The surgical system may include a XR headset controller 410 that may at least partially reside in the XR headset 150, the computer platform 400, and/or in another system component connected via wired cables and/or wireless communication links. Various functionality is provided by software executed by the XR headset controller 410. The XR headset controller 410 is configured to receive information from the camera tracking system 200 and the navigation controller 404, and to generate an XR image based on the information for display on the display device 438.

The XR headset controller 410 can be configured to operationally process frames of tracking data from tracking cameras from the cameras 430 (tracking cameras), signals from the microphone 1620, and/or information from the pose sensor 436 and the gesture sensor 434, to generate information for display as XR images on the display device 438 and/or as other for display on other display devices for user viewing. Thus, the XR headset controller 410 illustrated as a circuit block within the XR headset 150 is to be understood as being operationally connected to other illustrated components of the XR headset 150 but not necessarily residing within a common housing or being otherwise transportable by the user. For example, the XR headset controller 410 may reside within the computer platform 400 which, in turn, may reside within the cabinet 330 of the camera tracking system 200, the cabinet 106 of the surgical robot 100, etc.

6. REFERENCES

A listing of references cited herein follows:
1. Armanious, K., Jiang, C., Abdulatif, S., Küstner, T., Gatidis, S., Yang, B.: Unsupervised medical image translation using Cycle-MeDGAN. European Signal Processing Conference 2019-September (2019).
2. Chartsias, A., Joyce, T., Dharmakumar, R., Tsaftaris, S. A.: Adversarial image synthesis for unpaired multi-modal cardiac data. In: Tsaftaris, S. A., Gooya, A., Frangi, A. F., Prince, J. L. (eds.) Simulation and Synthesis in Medical Imaging. pp. 3-13. Springer International Publishing, Cham (2017)
3. Chong, M. J., Forsyth, D.: Gans n' roses: Stable, controllable, diverse image to image translation (works for videos too!) (2021)
4. Chu, C., Zhmoginov, A., Sandler, M.: Cyclegan, a master of steganography. arXiv preprint arXiv:1712.02950 (2017)
5. Florkow, M. C., Zijlstra, F., Willemsen, K., Maspero, M., van den Berg, C. A. T., Kerkmeijer, L. G. W., Castelein, R. M., Weinans, H., Viergever, M. A., van Stralen, M., Seevinck, P. R.: Deep learning-based mr-to-ct synthesis: The influence of varying gradient echo-based mr images as input channels. Magnetic Resonance in Medicine 83(4), 1429-1441 (2020)
6. Gilad, I., Nissan, M.: Sagittal evaluation of elemental geometrical dimensions of human vertebrae. Journal of anatomy 143, 115 (1985)
7. Hiasa, Y., Otake, Y., Takao, M., Matsuoka, T., Takashima, K., Carass, A., Prince, J. L., Sugano, N., Sato, Y.: Cross-modality image synthesis from unpaired data using cyclegan: Effects of gradient consistency loss and training data size. Lecture Notes in Computer Science (including subseries Lecture Notes in Artificial Intelligence and Lecture Notes in Bioinformatics) 11037 LNCS, 31-41(2018)
8. Karthik, E. M. N., Laporte, C., Cheriet, F.: Three-dimensional segmentation of the scoliotic spine from mri using unsupervised volume-based mr-ct synthesis. In: Medical Imaging 2021: Image Processing. vol. 11596, p. 11596111. International Society for Optics and Photonics (2021)
9. Pang, S., Pang, C., Zhao, L., Chen, Y., Su, Z., Zhou, Y., Huang, M., Yang, W., Lu, H., Feng, Q.: Spineparsenet: Spine parsing for volumetric mr image by a two-stage segmentation framework with semantic image representation. IEEE Transactions on Medical Imaging 40(1), 262-273 (2021). https://doi.org/10.1109/TMI.2020.3025087
10. Park, T., Efros, A. A., Zhang, R., Zhu, J. Y.: Contrastive learning for unpaired image-to-image translation. In: European Conference on Computer Vision (2020)
11. Sekuboyina, A., et al.: Verse: A vertebrae labelling and segmentation benchmark for multi-detector ct images. Medical Image Analysis 73, 102166 (2021). https://doi.org/https://doi.org/10.1016/j.media.2021.102166, https://www.sciencedirect.com/science/article/pii/S1361841521002127
12. Staartjes, V. E., Seevinck, P. R., Vandertop, W. P., van Stralen, M., Schroder, M. L.: Magnetic resonance imaging-based synthetic computed tomography of the lumbar spine for surgical planning: a clinical proof-of-concept. Neurosurgical Focus FOC 50(1), E13 (2021)
13. Tang, B., Wu, F., Fu, Y., Wang, X., Wang, P., Orlandini, L. C., Li, J., Hou, Q.: Dosimetric evaluation of synthetic ct image generated using a neural network for mr-only brain radiotherapy. Journal of Applied Clinical Medical Physics 22(3), 55-62 (2021)
14. Tomar, D., Zhang, L., Portenier, T., Goksel, O.: Content-preserving unpaired translation from simulated to realistic ultrasound images. In: de Bruijne, M., Cattin, P. C., Cotin, S., Padoy, N., Speidel, S., Zheng, Y., Essert, C. (eds.) Medical Image Computing and Computer Assisted Intervention—MICCAI 2021. pp. 659-669. Springer International Publishing, Cham (2021)
15. Wolterink, J. M., Dinkla, A. M., Savenij e, M. H. F., Seevinck, P. R., van den Berg, C. A. T., Išgum, I.: Deep mr to ct synthesis using unpaired data. In: Tsaftaris, S. A., Gooya, A., Frangi, A. F., Prince, J. L. (eds.) Simulation and Synthesis in Medical Imaging. pp. 14-23. Springer International Publishing, Cham (2017)
16. Yang, H., Sun, J., Carass, A., Zhao, C., Lee, J., Xu, Z., Prince, J.: Unpaired brain mr-to-ct synthesis using a structure-constrained cyclegan. In: Deep Learning in Medical Image Analysis and Multimodal Learning for Clinical Decision Support, pp. 174-182. Springer (2018)
17. Zhang, Z., Yang, L., Zheng, Y.: Translating and segmenting multimodal medical volumes with cycle- and shape-consistency generative adversarial network. In: Proceedings of the IEEE conference on computer vision and pattern Recognition. pp. 9242-9251 (2018)
18. Zhu, J. Y., Park, T., Isola, P., Efros, A. A.: Unpaired image-to-image translation using cycle-consistent adversarial networks. In: Computer Vision (ICCV), 2017 IEEE International Conference on (2017)
19. Zijlstra, F., Willemsen, K., Florkow, M. C., Sakkers, R. J., Weinans, H. H., van der Wal, B. C., van Stralen, M., Seevinck, P. R.: Ct synthesis from MR images for orthopedic applications in the lower arm using a conditional generative adversarial network. In: Medical Imaging 2019: Image Processing. vol. 10949, pp. 387-393. SPIE (2019)

What is claimed is:
1. A method comprising:
transforming pre-operative images of a patient obtained from a first imaging modality to an estimate of the pre-operative images of the patient in a second imaging modality that is different than the first imaging modality; and
registering the estimate of the pre-operative images of the patient in the second imaging modality to intra-operative navigable images or data of the patient,
wherein the transforming of the pre-operative images of the patient obtained from the first imaging modality to the estimate of the pre-operative images of the patient in the second imaging modality, comprises:
encoding pre-operative image of the patient obtained from the first imaging modality to output a content vector indicating where anatomical features are located in the pre-operative images of the first imaging modality;
encoding pre-operative images of the patient obtained from the second imaging modality to output a style vector indicating how the anatomical features look in the pre-operative images of the second imaging modality; and
decoding the content vector indicating where the anatomical features are located in the pre-operative images of the first imaging modality using the style vector indicating how the anatomical features look in the pre-operative images of the second imaging modality; and generating the estimate of the pre-operative images of the patient in the second imaging modality based on an output of the decoding.

2. The method of claim 1, wherein the transforming of the pre-operative images of the patient obtained from the first imaging modality to the estimate of the pre-operative images of the patient in the second imaging modality, comprises:
processing the pre-operative images of the patient obtained from the first imaging modality through a neural networks model configured to transform pre-operative images in the first imaging modality to estimates of the pre-operative images in the second imaging modality, wherein the neural networks model has been trained based on matched sets of training images containing anatomical features captured by the first imaging modality and training images containing anatomical features captured by the second imaging modality, wherein at least some of the anatomical features captured by the first imaging modality correspond to at least some of the anatomical features captured by the second imaging modality.

3. The method of claim 2, further comprising:
performing the training of the neural networks model based on matched sets of training images containing anatomical features captured by the first imaging modality and training images containing anatomical features captured by the second imaging modality.

4. The method of claim 1, wherein:
the transforming of the pre-operative images of the patient obtained from the first imaging modality to the estimate of the pre-operative images of the patient in the second imaging modality, comprises transforming pre-operative magnetic resonance imaging (MRI) images of the patient to synthetic x-ray images of the patient; and
the registering comprises registering the synthetic x-ray images of the patient to intraoperative navigable x-ray images of the patient, wherein the intra-operative navigable x-ray images are registered to a coordinate system of a camera tracking system.

5. The method of claim 4, wherein the transforming of the pre-operative MRI images of the patient to the synthetic x-ray images of the patient, comprises:
transforming the pre-operative MRI images of the patient to synthetic computerized tomography (CT) images of the patient; and
transforming the synthetic CT images of the patient to the synthetic x-ray images.

6. The method of claim 5, wherein the transforming of the pre-operative MRI images of the patient to the synthetic CT images of the patient, comprises:
processing the pre-operative MRI images of the patient through a neural networks model configured to transform pre-operative MRI images to synthetic CT images, wherein the neural networks model has been trained based on matched sets of training MRI images containing anatomical features captured by MRI modality and training CT images containing anatomical features captured by CT imaging modality, wherein at least some of the anatomical features captured by the MRI modality correspond to at least some of the anatomical features captured by the CT imaging modality.

7. The method of claim 5, further comprising:
obtain a first slice set of pre-operative MRI images of the patient having higher resolution in a first plane and a lower resolution in a second plane orthogonal to the first plane;
obtain a second slice set of pre-operative MRI image slices of the patient having higher resolution in the second plane and a lower resolution in the first plane;
merging the first and second slice sets of pre-operative MRI images by registration of anatomical features captured in both of the the first and second slice sets of pre-operative MRI images, to output a merged slice set of pre-operative MRI images,
wherein the merged slice set of pre-operative MRI images are processed through the neural networks model for transform to the synthetic CT images.

8. The method of claim 1, wherein:
the transforming of the pre-operative images of the patient obtained from the first imaging modality to the estimate of the pre-operative images of the patient in the second imaging modality, comprises transforming pre-operative magnetic resonance imaging (MRI) images or computerized tomography (CT) images of the patient to synthetic ultrasound images of the patient; and
the registering comprises registering the synthetic ultrasound images to intra-operative navigable ultrasound images of the patient, wherein the intra-operative navigable ultrasound images are registered to a coordinate system of a camera tracking system.

9. The method of claim 8, wherein the transforming of the pre-operative magnetic resonance imaging (MRI) images or the computerized tomography (CT) images of the patient to the synthetic ultrasound images of the patient, comprises:
processing the pre-operative MRI images or CT images of the patient through a neural networks model configured to transform pre-operative MRI images or CT images to synthetic ultrasound images, wherein the neural networks model has been trained based on matched sets of: 1) training ultrasound images; and 2) either training MRI images or training CT images,
wherein the matched sets of: 1) training ultrasound images; and 2) either training MRI images or training CT images, have defined correspondences between anatomical features captured in images of the matched sets.

10. The method of claim 1, wherein:
the transforming of the pre-operative images of the patient obtained from the first imaging modality to the estimate of the pre-operative images of the patient in the second imaging modality, comprises transforming pre-operative magnetic resonance imaging (MRI) images or computerized tomography (CT) images of the patient to synthetic optical camera images of the patient; and
the registering comprises registering the synthetic optical camera images to intraoperative navigable optical camera images of the patient, wherein the intra-operative navigable optical camera images are registered to a coordinate system of a camera tracking system.

11. The method of claim 10, wherein the transforming of the pre-operative magnetic resonance imaging (MRI) images or computerized tomography (CT) images of the patient to the synthetic optical camera images of the patient, comprises:
processing the pre-operative MRI images or CT images of the patient through a neural networks model configured to transform pre-operative MRI images or CT images to synthetic optical camera images, wherein the neural networks model has been trained based on matched sets of: 1) training optical camera images; and 2) either training MRI images or training CT images,
wherein the matched sets of: 1) training optical camera images; and 2) either training MRI images or training CT images, have defined correspondences between anatomical features captured in images of the matched sets.

12. The method of claim 1, wherein: the first and second imaging modalities are different ones of: magnetic resonance imaging (MRI) modality; computerized tomography (CT) imaging modality; and ultrasound imaging modality.

13. The method of claim 1, wherein: the encoding of the pre-operative image of the patient obtained from the first imaging modality to output the content vector indicating where anatomical features are located in the preoperative images of the first imaging modality, comprises processing the pre-operative image of the patient in the first imaging modality through a first neural networks model configured to output the content vector indicating where anatomical features are located in the pre-operative images of the first imaging modality; the encoding of the pre-operative images of the patient obtained from the second imaging modality to output the style vector indicating how the anatomical features look in the preoperative images of the second imaging modality, comprises processing the pre-operative images of the patient obtained from the second imaging modality through a second neural networks model configured to output the style vector indicating how the anatomical features look in the pre-operative images of the second imaging modality; and the decoding of the content vector indicating where the anatomical features are located in the pre-operative images of the first imaging modality using the style vector indicating how the anatomical features look in the pre-operative images of the second imaging modality, comprises processing the content vector and the style vector through a third neural networks model configured to output the estimate of the pre-operative images of the patient in the second imaging modality.

14. The method of claim 13, further comprising:
performing training of the first and second neural networks model,
wherein the training alternates between a training cycle using a style consistency loss operation to train based on differences in content between the pre-operative image from the first and second imaging modalities and another training cycle using a content consistency loss operation to train based on differences in style between the pre-operative image from the first and second imaging modalities.

15. The method of claim 13, further comprising:
processing the estimate of the pre-operative images of the patient in the second imaging modality through a fourth neural networks model configured to detect keypoints in the preoperative images of the patient in the second imaging modality; and
tuning parameters of the second neural networks model based on the detected keypoints in the pre-operative images of the patient in the second imaging modality.

16. A computer platform for computer assisted navigation during surgery, comprising at least one processor operative to:
transform pre-operative images of a patient obtained from a first imaging modality to an estimate of the pre-operative images of the patient in a second imaging modality that is different than the first imaging modality; and
register the estimate of the pre-operative images of the patient in the second imaging modality to intra-operative navigable images or data of the patient, wherein the transformation of the preoperative images of the patient obtained from the first imaging modality to the estimate of the pre-operative images of the patient in the second imaging modality, comprises to:
encode pre-operative image of the patient obtained from the first imaging modality to output a content vector indicating where anatomical features are located in the pre-operative images of the first imaging modality;
encode pre-operative images of the patient obtained from the second imaging modality to output a style vector indicating how the anatomical features look in the pre-operative images of the second imaging modality; and
decode the content vector indicating where the anatomical features are located in the preoperative images of the first imaging modality using the style vector indicating how the anatomical features look in the pre-operative images of the second imaging modality; and
generate the estimate of the pre-operative images of the patient in the second imaging modality based on an output of the decoding.

17. The computer platform of claim 16, wherein the transformation of the preoperative images of the patient obtained from the first imaging modality to the estimate of the pre-operative images of the patient in the second imaging modality, comprises to:
process the pre-operative images of the patient obtained from the first imaging modality through a neural networks model configured to transform pre-operative images in the first imaging modality to estimates of the pre-operative images in the second imaging modality, wherein the neural networks model has been trained based on matched sets of training images containing anatomical features captured by the first imaging modality and training images containing anatomical features captured by the second imaging modality, wherein at least some of the anatomical features captured by the first imaging modality correspond to at least some of the anatomical features captured by the second imaging modality.

18. The computer platform of claim 16, wherein: the encoding of the pre-operative image of the patient obtained from the first imaging modality to output the content vector indicating where anatomical features are located in the preoperative images of the first imaging modality, comprises to process the pre-operative image of the patient in the first imaging modality through a first neural networks model configured to output the content vector indicating where anatomical features are located in the pre-operative images of the first imaging modality; the encoding of the pre-operative images of the patient obtained from the second imaging modality to output the style vector indicating how the anatomical features look in the preoperative images of the second imaging modality, comprises to process the pre-operative images of the patient obtained from the second imaging modality through a second neural networks model configured to output the style vector indicating how the anatomical features look in the pre-operative images of the second imaging modality; and the decoding of the content vector indicating where the anatomical features are located in the pre-operative images of the first imaging modality using the style vector indicating how the anatomical features look in the pre-operative images of the second imaging modality, comprises to process the content vector and the style vector through a third neural networks model configured to output the estimate of the pre-operative images of the patient in the second imaging modality.

* * * * *